US006953573B1

(12) United States Patent  (10) Patent No.: US 6,953,573 B1
Cheever et al.  (45) Date of Patent: Oct. 11, 2005

(54) COMPOUNDS FOR ELICITING OR ENHANCING IMMUNE REACTIVITY TO HER-2/NEU PROTEIN FOR PREVENTION OR TREATMENT OF MALIGNANCIES IN WHICH THE HER-2/NEU ONCOGENE IS ASSOCIATED

(75) Inventors: Martin A. Cheever, Mercer Island, WA (US); Mary L. Disis, Renton, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/167,516

(22) Filed: Oct. 6, 1998

Related U.S. Application Data

(63) Continuation of application No. 08/625,101, filed on Apr. 1, 1996, now Pat. No. 5,869,445, which is a continuation-in-part of application No. 08/414,417, filed on Mar. 31, 1995, now Pat. No. 5,801,005, which is a continuation-in-part of application No. 08/106,112, filed on Aug. 12, 1993, now abandoned, which is a continuation-in-part of application No. 08/033,644, filed on Mar. 17, 1993, now abandoned.

(51) Int. Cl.[7] .......................... A61K 35/14; C12N 15/85
(52) U.S. Cl. .................................. 424/93.21; 424/93.71
(58) Field of Search ........................... 424/93.21, 93.71; 514/44; 536/23.5, 23.4

(56) References Cited

U.S. PATENT DOCUMENTS

| 3,766,162 A | 10/1973 | Spector .................. 260/112 R |
| 3,791,932 A | 2/1974 | Schuurs et al. ........ 195/103.5 R |
| 3,817,837 A | 6/1974 | Rubenstein et al. ... 195/103.5 R |
| 3,850,752 A | 11/1974 | Schuurs et al. ........ 195/103.5 R |
| 3,901,654 A | 8/1975 | Gross ........................ 23/230 B |
| 3,935,074 A | 1/1976 | Rubenstein et al. ... 195/103.5 R |
| 3,984,533 A | 10/1976 | Uzgiris ......................... 424/12 |
| 3,996,345 A | 12/1976 | Ullman et al. ................ 424/12 |
| 4,034,074 A | 7/1977 | Miles ............................. 424/1 |
| 4,098,876 A | 7/1978 | Piasio et al. .................... 424/1 |
| 4,233,402 A | 11/1980 | Maggio et al. ................ 435/7 |
| 4,452,901 A | 6/1984 | Gordon et al. .............. 436/506 |
| 5,320,947 A | 6/1994 | Cheever et al. ............... 435/29 |
| 5,401,638 A | 3/1995 | Carney et al. ............. 435/7.23 |
| 5,693,522 A | * 12/1997 | Chada et al. |

FOREIGN PATENT DOCUMENTS

| WO | WO 90/14357 | 11/1990 |
| WO | WO 91/02062 | 2/1991 |

OTHER PUBLICATIONS

"Gene therapy", www.gateway.nlm.nih.gov, visited Jan. 23, 2004.*
Verma et al (Nature, 1997, vol. 389, pp. 239–242).*
Eck et al (Gene–Based Therapy, In: The Pharmacological Basis of Therapeutics, Goodman and Gilman, Ed.s, 1996, pp. 77–101).*
Orkin et al state ("Report and Recommendation of the Panel to Assess the NIH Investment in Research on Gene Therapy", NIH, 1995).*
Davis et al, "Plasmid DNA is superior to viral vectors for direct gene transfer into adult mouse skeletal muscle", Hum Gene Ther, vol. 4, pp. 733–740, Dec. 1993.*
Wickham, T.J., "Targeting Adenovirus", Gene therapy, vol. 7, pp. 110–114, Jan. 2000.*
Crystal, R.G., "In vivo and ex vivo gene therapy strategies to treat tumors using adenovirus gene transfer vectors", Cancer chemotherapy and Pharmacology, vol. 43, Suppl., pp. S90–S99, May 1999.*
Yamamoto et al., "Similarity of protein encoded by the c–erb–B–2 gene to epidermal growth factor receptor," *Nature* 319: 230–234, 1986.
Zabrecky et al., "The Extracellular Domain of p185/neu Is Released from the Surface of Human Breast Carcinoma Cells, SK–BR–3," *Journal of Biological Chemistry* 266(3): 1716–1720, 1991.
Press et al., "Expression of the HER–2/neu proto–oncogene in normal human adult and fetal tissues," *Oncogene* 5: 953–962, 1990.
Raines and Ross, "Platelet–derived Growth Factor. I. High Yields Purification and Evidence for Multiple Forms," *Journal of Biological Chemistry* 257(9): 5154–5159, 1982.
Riberdy and Cresswell, "The Antigen–Processing Mutant T2 Suggests a Role for MHC–Linked Genes in Class II Antigen Presentation," *Journal of Immunology* 148(8):2586–2590, 1992.
Rothbard and Taylor, "A sequence pattern common to T cell epitopes," *EMBO Journal* 7(1): 93–100, 1988.
Semba et al., "A v–erbB–related protooncogene, c–erbB–2, is distinct from the c–erbB–1/epidermal growth factor–receptor gene and is amplified in a human salivary gland adenocarcinoma," *Proc. Natl. Acad. Sci. USA* 82: 6497–6501, 1985.
Spies et al., "A gene in the human major histocompatibility complex class II region controlling the class I antigen presentation pathway," *Nature* 348: 744–747, 1990.
Stern et al., "Oncogene Activation of p185(neu) Stimulates Tyrosine Phosphorylation In Vivo," *Molecular and Cellular Biology* 8(9): 3969–3973, 1988.
Trowsdale et al., "Sequence encoded in the class II region of the MHC related to the 'ABC' superfamily of transporters," *Nature* 348: 741–744, 1990.
Weiner et al., "A point mutation in the neu oncogene mimics ligand induction of receptor aggregation," *Nature* 339: 230–231, 1989.

(Continued)

*Primary Examiner*—Karen A. Canella
(74) *Attorney, Agent, or Firm*—Seed IP Law Group PLLC

(57) ABSTRACT

Compounds and compositions for eliciting or enhancing immune reactivity to HER-2/neu protein are disclosed. The compounds include polypeptides and nucleic acid molecules encoding such peptides. The compounds may be used for the prevention or treatment of malignancies in which the HER-2/neu oncogene is associated.

3 Claims, 4 Drawing Sheets

OTHER PUBLICATIONS

Wide, L., "Solid Phase Antigen–Antibody Systems," in Radioimmunoassay Methods, Kirkham and Hunter (ed.), 1973, pp. 405–412.

Wisdom, G.B., "Enzyme–Immunoassay," *Clin. Chem.* 22(8): 1243–1255, 1976.

Leitzel et al., "Elevated Soluble c–erbB2 Antigen Levels in the Serum and Effusions of a Proportion of Breast Cancer Patients," *Journal of Clinical Oncology 10*(9): 1436–1443, 1992.

Lichtenstein et al., "Effects of .beta.–2 Microglobulin Anti-sense oligonucleotides on Sensitivity of HER2/neu Oncogene–Expressing and Nonexpressing Target Cells to Lymphocyte–Mediated Lysis," *Cellular Immunology 141*: 219–232, 1992.

Lippman, M., "Potential Contributions of Breast Cancer Biology to Management of Breast Cancer," *Advances in Oncology 8*(3): 26–28, 1992.

Maguire and Greene, "The neu (c–erbB–2) Oncogene," *Seminars in Oncology 16*(2): 148–155, 1989.

Margalit et al., "Prediction Of Immunodominant Helper T Cell Antigenic Sites From The Primary Sequence," *Journal of Immunology 138*(7): 2213–2229, 1987.

McGlynn et al., "Large–scale purification and characterisation of a recombinant epidermal growth–factor receptor protein–tyrosine kinase. Modulation of activity by multiple factors," *Eur. J. Biochem. 207*: 265–275, 1992.

McKenzie et al., "Induction of Antitumor Immunity by Immunization with a Vaccinia Virus Vector Expressing and Oncogene–encoded Product," in Vaccines 88, Cold Spring Harbor Laboratory, 1988, pp. 19–23.

Mietzner et al., "Purification and Characterization of the Major Iron–Regulated Protein Expressed By Pathogenic Neisseriae," *Journal of Experimental Medicine 165*: 1041–1057, 1987.

Mori et al., "In Vitro and in vivo Release of Soluble erbB–2 Protein from Human Carcinoma Cells," *Japanese Journal of Cancer Research 81*: 489–494, 1900.

Paik et al., "Pathologic Findings From the National Surgical Adjuvant Breast and Bowel Project: Prognostic Significance of erbB–2 Protein Overexpression in Primary Breast Cancer," *Journal of Clinical Oncology 8*(1): 103–112, 1990.

Parker et al., "Sequence Motifs Important For Peptide Binding To The Human MHC Class I Molecule, HLA–A2," *Journal of Immunology 149*(11): 3580–3587, 1992.

Flanagan and Leder, "neu protoncogene fused to an immunoglobulin heavy chain gene requires immunoglobulin light chain for cell surface expression and oncogenic transformation," *Proc. Natl. Acad. Sci. USA 85*: 8057–8061, 1998.

Igelhart et al., "Increased erbB–2 Gene Copies and Expression in Multiple States of Breast Cancer," *Cancer Research 50*: 6701–6707, 1990.

Ioannides et al., "Antigens Recognized by T cells in Ovarian Cancer," in Abstracts of the Fourth International Conference of Anticancer Research, Oct. 21–25, 1992, Rethymnon, Crete, Greece, p. 1870.

Ioannides et al., "CTL Clones Isolated from Ovarian Tumor Infiltrating Lymphocytes can Recognize Peptides with Sequence Corresponding to the HER2/neu Gene Product," *FASEB Journal 6*: A1404, Abstract No. 2711, 1992.

Ioannides et al., "Cytotoxic T Cells Isolated From Ovarian Malignant Ascites Recognize a Peptide Derived From the HER–2/neu Proto–oncogene," *Cell. Immunol. 151*: 225–234, 1993.

Ioannides et al., "Cytotoxic T–Cell Clones Isolated from Ovarian Tumour Infiltrating Lymphocytes Recognize Common Determinants on Non–Ovarian Tumour Clones," *Scand. J. Immunol. 37*: 413–424, 1993.

Ioannides et al., "T–Cell Recognition of Oncogene Products: A New Strategy for Immunotherapy," *Molecular Carcinogenesis 6*: 77–82, 1992.

Ioannides, "Antigens and vaccines of female genital cancers (Meeting abstract)," Cancerlit Database Abstract No. ICDB/93690682, 1992.

Kallioniemi et al., "ERBB2 amplification in breast cancer analyzed by fluorescence in situ hybridization," *Proc. Natl. Acad. Sci. 89*: 5321–5325, 1992.

Kerns et al., "c–erbB–2 Expression In Breast Cancer Detected by Immunoblotting and Immunohistochemistry," *Journal of Histochemistry and Cytochemistry 38*(12): 1823–1830, 1990.

Laemmli, U., "Cleavage of Structural Proteins during the Assembly of the Head of Bacteriophage T4," *Nature 227*: 680–685, 1970.

Bodmer, W., "T–Cell Immune Responses to Cancer—A New Look," *Human Immunology 30*:259–261, 1991.

Bowen–Pope et al., "Production of platelet–derived growth factor–like molecules and reduced expression of platelet–derived growth factor receptors accompany transformation by a wide spectrum of agents," *Proc. Natl. Acad. Sci. USA 81*: 2396–2400, 1984.

Brooks et al., "Human lymphocyte markers defined by antibodies derived from somatic cell hybrids," *Clin. Exp. Immunol. 39*: 477–485, 1980.

Brown et al., "Protein Antigens of Normal and Malignant Human Cells Identified by Immunoprecipitation with Monoclonal Antibodies," *Journal of Biological Chemistry 255*(11): 4980–4983, 1980.

Burnette et al., "Western Blotting: Electrophoretic Transfer of Proteins from Sodium Dodecyl Sulfate–Polyacrylamide Gels to Unmodified Nitrocellulose and Radiographic Detection with Antibody and Radioiodinated Protein A," *Analytical Biochemistry 112*: 195–203, 1981.

Coussens et al., "Tyrosine Kinase Receptor with Extensive Homology to EGF Receptor Shares Chromosomal Location with neu Oncogene," *Science 230*: 1132–1139, 1985.

Dhut et al, "BCR–ABL and BCR Proteins: Biochemical Characterization and Localization," *Leukemia 4*(11): 745–750, 1990.

Disis et al., "Existent T–Cell and Antibody Immunity to HER–2/neu Protein in Patients With Breast Cancer," *Cancer Res. 54*: 16–20, 1994.

Falk et al., "Allele–specific motifs revealed by sequencing of self–peptides eluted from MHC molecules," *Nature 351*: 290–296, 1991.

Feller and de la Cruz, "Identifying antigenic T–cell sites," *Nature 349*: 720–721, 1991.

Fisk et al., "Oligopeptide Induction of a Cytotoxic T Lymphocyte Response to HER–2/Neu Proto–oncogenes in Vitro," *Cellular Immunology 157*:415–427, 1994.

Ben–Mahrez et al., "Circulating Antibodies Against C–myc Oncogene Product In Sera Of Colorectal Cancer Patients," *Int. J. Cancer 46*: 35–38, 1990.

Ben–Mahrez et al., "Detection of circulating antibodies against c–myc protein in cancer patient sera," *Br. J. Cancer 57*: 529–534, 1988.

Bishop and Orosz, "Limiting Dilution Analysis For Alloreactive, TCGF–Secretory T Cells. Two Related LDA Methods That Discriminate Between Unstimulated Precursor T Cells and In Vivo–Alloactivated T Cells," *Transplantation 47*(4): 671–677, 1989.

Alper et al., "The Presence of c–erbB–2 Gene Product–related Protein in Culture Medium Contitioned by Breast Cancer Cell Line SK–BR–3," *Cell Growth & Differentiation 1*:591–599, 1990.

Bargmann et al., "The neu oncogene encodes an epidermal growth factor receptor–related protein," *Nature 319*:226–230, 1986.

Baselga et al., "Phase II Study of Weekly Intravenous Recombinant Humanized Anti–p185(HER2) Monoclonal Antibody in Patients With HER2/neu–Overexpressing Metastatic Breast Cancer," *Journal of Clinical Oncology 14*(3): 737–744, 1996.

* cited by examiner

COMPOUNDS FOR ELICITING OR ENHANCING IMMUNE REACTIVITY TO HER-2/NEU PROTEIN FOR PREVENTION OR TREATMENT OF MALIGNANCIES IN WHICH THE HER-2/NEU ONCOGENE IS ASSOCIATED

CROSS REFERENCE TO RELATED APPLICATION

This application is a continuation of U.S. patent application Ser. No. 08/625,101, filed Apr. 1, 1996, which issued as U.S. Pat. No. 5,869,445; which application is a continuation-in-part of U.S. patent application Ser. No. 08/414,417, filed Mar. 31, 1995, which issued as U.S. Pat. No. 5,801,005; which application is a continuation-in-part of U.S. patent application Ser. No. 08/106,112, filed on Aug. 12, 1993, abandoned; which application is a continuation-in-part of U.S. patent application Ser. No. 08/033,644, filed Mar. 17, 1993, abandoned.

TECHNICAL FIELD

The present invention is generally directed toward polypeptides, and nucleic acid molecules encoding such polypeptides, for eliciting or enhancing an immune response to HER-2/neu protein, including for use in the treatment of malignancies in which the HER-2/neu oncogene is associated.

BACKGROUND OF THE INVENTION

Despite enormous investments of financial and human resources, cancer remains one of the major causes of death. For example, cancer is the leading cause of death in women between the ages of 35 and 74. Breast cancer is the most common malignancy in women and the incidence for developing breast cancer is on the rise. One in nine women will be diagnosed with the disease. Standard approaches to cure breast cancer have centered around a combination of surgery, radiation and chemotherapy. These approaches have resulted in some dramatic successes in certain malignancies. However, these approaches have not been successful for all malignancies and breast cancer is most often incurable when attempting to treat beyond a certain stage. Alternative approaches to prevention and therapy are necessary.

A common characteristic of malignancies is uncontrolled cell growth. Cancer cells appear to have undergone a process of transformation from the normal phenotype to a malignant phenotype capable of autonomous growth. Amplification and overexpression of somatic cell genes is considered to be a common primary event that results in the transformation of normal cells to malignant cells. The malignant phenotypic characteristics encoded by the oncogenic genes are passed on during cell division to the progeny of the transformed cells.

Ongoing research involving oncogenes has identified at least forty oncogenes operative in malignant cells and responsible for, or associated with, transformation. Oncogenes have been classified into different groups based on the putative function or location of their gene products (such as the protein expressed by the oncogene).

Oncogenes are believed to be essential for certain aspects of normal cellular physiology. In this regard, the HER-2/neu oncogene is a member of the tyrosine protein kinase family of oncogenes and shares a high degree of homology with the epidermal growth factor receptor. HER-2/neu presumably plays a role in cell growth and/or differentiation. HER-2/neu appears to induce malignancies through quantitative mechanisms that result from increased or deregulated expression of an essentially normal gene product.

HER-2/neu (p185) is the protein product of the HER-2/neu oncogene. The HER-2/neu gene is amplified and the HER-2/neu protein is overexpressed in a variety of cancers including breast, ovarian, colon, lung and prostate cancer. HER-2/neu is related to malignant transformation. It is found in 50%–60% of ductal in situ carcinoma and 20%–40% of all breast cancers, as well as a substantial fraction of adenocarcinomas arising in the ovaries, prostate, colon and lung. HER-2/neu is intimately associated not only with the malignant phenotype, but also with the aggressiveness of the malignancy, being found in one-fourth of all invasive breast cancers. HER-2/neu overexpression is correlated with a poor prognosis in both breast and ovarian cancer. HER-2/neu is a transmembrane protein with a relative molecular mass of 185 kd that is approximately 1255 amino acids (aa) in length. It has an extracellular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 aa with 80% homology to EGFR.

Due to the difficulties in the current approaches to therapy of cancers in which the HER-2/neu oncogene is associated, there is a need in the art for improved compounds and compositions. The present invention fulfills this need, and further provides other related advantages.

SUMMARY OF THE INVENTION

Briefly stated, the present invention provides polypeptides, nucleic acid molecules (directing the expression of such polypeptides) and viral vectors (directing the expression of such polypeptides) for uses which include the immunization of a warm-blooded animal against a malignancy in which the HER-2/neu oncogene is associated. A polypeptide or nucleic acid molecule according to this invention may be present in a composition that includes a pharmaceutically acceptable carrier or diluent. Such a polypeptide, nucleic acid molecule, viral vector or pharmaceutical composition may be administered on a one-time basis (e.g., when a malignancy is suspected) or on a periodic basis (e.g., for an individual with an elevated risk of acquiring or reacquiring a malignancy). A compound or composition of the present invention may be useful in the treatment of an existing tumor or to prevent tumor occurrence or reoccurrence.

In one aspect, the present invention provides compounds and compositions that elicit or enhance an immune response to HER-2/neu protein. One embodiment of the present invention provides a polypeptide encoded by a DNA sequence selected from: (a) nucleotides 2026 through 3765 of SEQ ID NO:1; and (b) DNA sequences that hybridize to a nucleotide sequence complementary to nucleotides 2026 through 3765 of SEQ ID No:1 under. moderately stringent conditions, wherein the DNA sequence encodes a polypeptide that produces an immune response to HER-2/neu protein. In a preferred embodiment, a polypeptide has the amino acid sequence of SEQ ID NO:2 from lysine, amino acid 676, through valine, amino acid 1255, or a variant thereof that produces at least an equivalent immune response. A composition is provided that comprises a polypeptide of the present invention in combination with a pharmaceutically acceptable carrier or diluent. In another embodiment, a nucleic acid molecule directing the expression of a polypeptide according to the present invention is provided. In another embodiment, a viral vector directing the expression of a polypeptide according to the present invention is provided.

In another aspect, the present invention provides a method for eliciting or enhancing an immune response to HER-2/neu protein, comprising administering to a warm-blooded animal (such as a human) in an amount effective to elicit or enhance the response a polypeptide according to the present invention, or a nucleic acid molecule or a viral vector, either directing the expression of such a polypeptide. In one embodiment, a peptide is administered in combination with a pharmaceutically acceptable carrier or diluent. In another embodiment, the step of administering comprises transfecting cells of the animal ex vivo with the nucleic acid molecule and subsequently delivering the transfected cells to the animal. In another embodiment, the step of administering comprises infecting cells of the animal ex vivo with the viral vector and subsequently delivering the infected cells to the animal.

These and other aspects of the present invention will become evident upon reference to the following detailed description and attached drawings.

DC+HER-2/neu polypeptide+CD4+/CD45RA+ T cells;

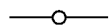

DC+CD4+/CD45RA+ T cells; and

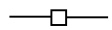

DC+HER-2/neu polypeptide.

Figure 1:
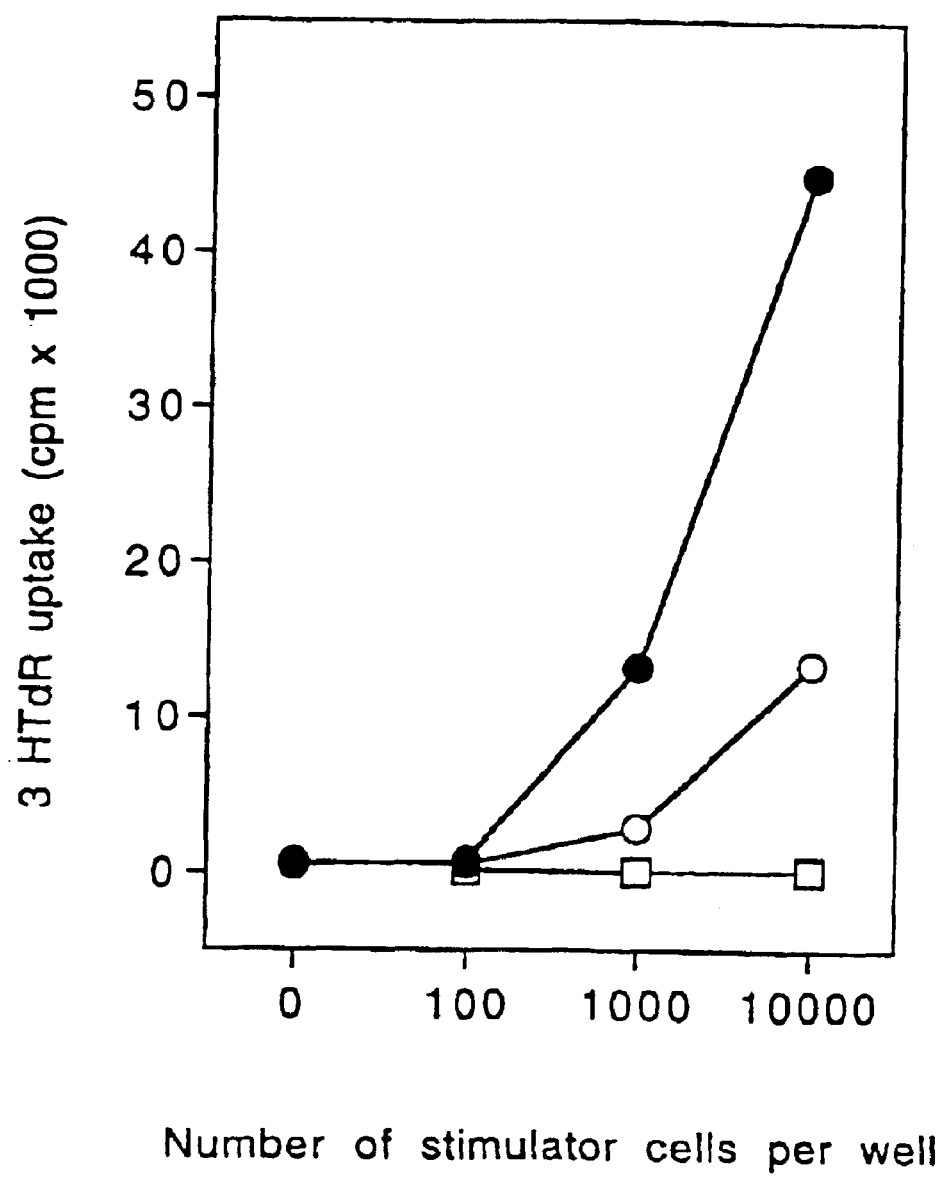
FIG. 1 shows the results of the priming of naive T lymphocytes to HER-2/neu polypeptide by dendritic cells. Bone marrow-derived DC were generated with GM-CSF and IL6 from CD34+ stem cells. DC pulsed with HER-2/neu polypeptide induced protein-specific proliferation of autologous CD4+/CD45RA+ T lymphocytes after 7 days of culturing T cells with DC. Bone marrow-derived CD34+ stem cells cultured for one week in serum-free medium containing GM-CSF and IL-6 were used as APC. APC were plated into 96-well round-bottomed plates (Corning, Corning, N.Y., USA) at various concentrations and incubated for 16–18 hours with 20–25 μg/ml of recombinant HER-2/neu polypeptide. CD4+ T lymphocytes were isolated from autologous peripheral blood mononuclear cells by positive selection using immunoaffinity columns (CellPro, Inc., Bothell, Wash., USA). Antigen-pulsed APC were irradiated (10 Gy), and CD4+ T lymphocytes were added at $10^5$ per well. Proliferative response of T cells was measured by the uptake of ($^3$H)thymidine (1 μCi/well) added on day 7 for 16–18 hours. Proliferation assays were performed in serum- and cytokine-free medium in 5 well replicates. The symbols represent.
Figure 2:
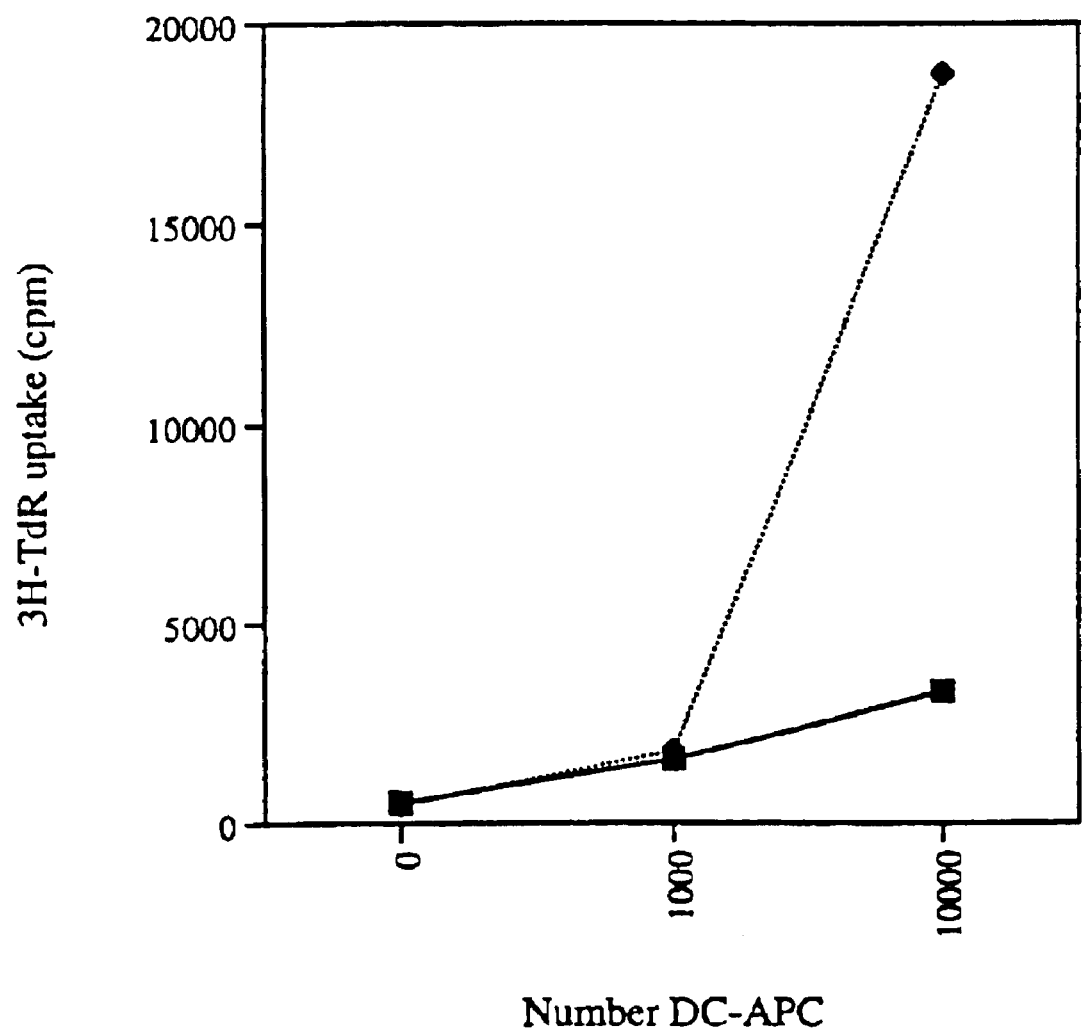

FIG. 2 shows the response of CD4+ cells to HER-2/neu polypeptide. Using the priming assay described for FIG. 1, CD4+ T cells from normal donors were tested for responses to recombinant human HER-2/neu polypeptide. The symbols represent:

SC+CD4; and

SC+CD4+HER-2/neu polypeptide. "SC" is stem cells.

Figure 3:
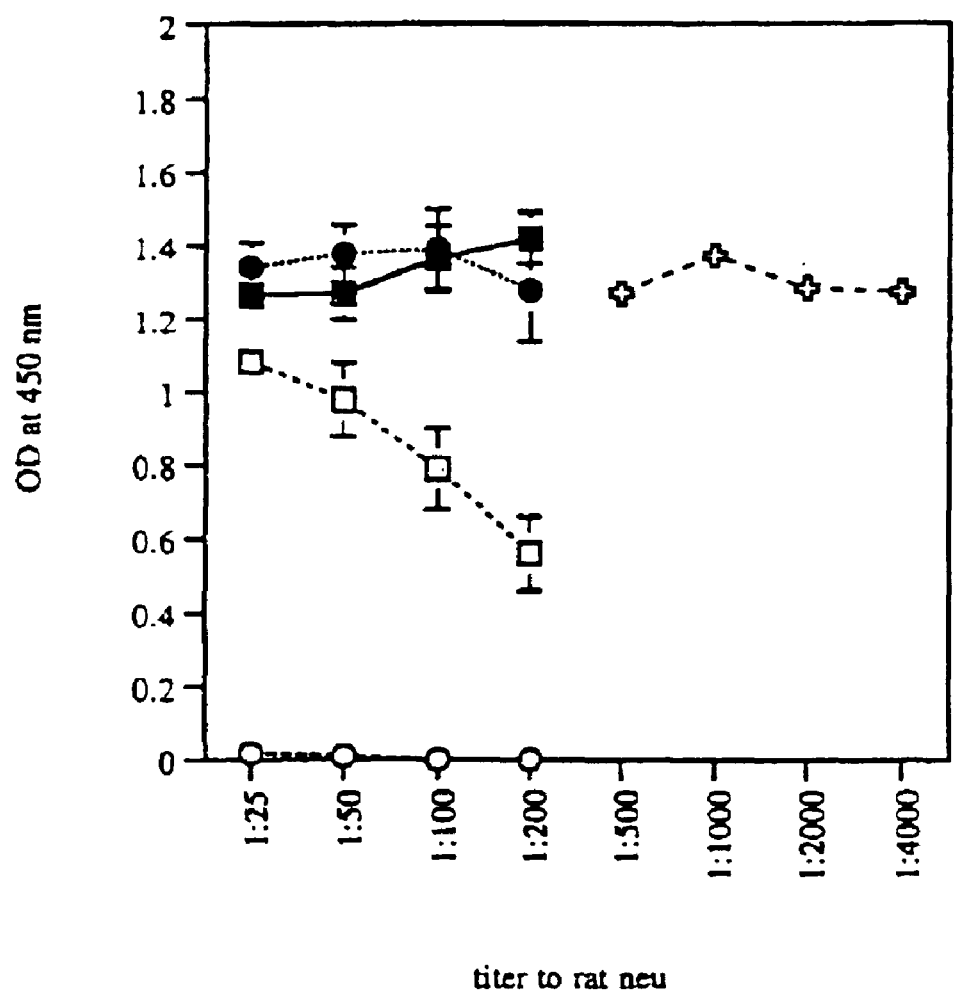

FIG. 3 shows that rats immunized with rat HER-2/neu polypeptide develop rat neu specific antibodies. Rats were immunized with recombinant rat HER-2/neu polypeptide 25 ug in MPL or vaccel adjuvant. Three immunizations were given, each 20 days apart. Twenty days after the final immunization rats were assessed for antibody responses to rat neu. Animals immunized with rat HER-2/neu polypeptide and the vaccel adjuvant showed high titer rat neu specific responses. The control was an animal immunized with human HER-2/neu polypeptide (foreign protein). In separate experiments, rats immunized with 100 ug and 300 ug of purified whole rat neu did not develop detectable neu specific antibodies (data not shown). Data represents the mean and standard deviation of 3 animals. The symbols represent:

rat HER-2/neu polypeptide/MPL; ······ ······ rat HER-2/neu polypeptide/vaccel;

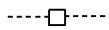

MPL alone;

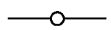

vaccel alone; and

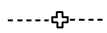

control. "MPL" and "vaccel" are adjuvants (Ribi, Bozeman, Mont., USA). "Neu" is HER-2/neu protein.

Figure 4:
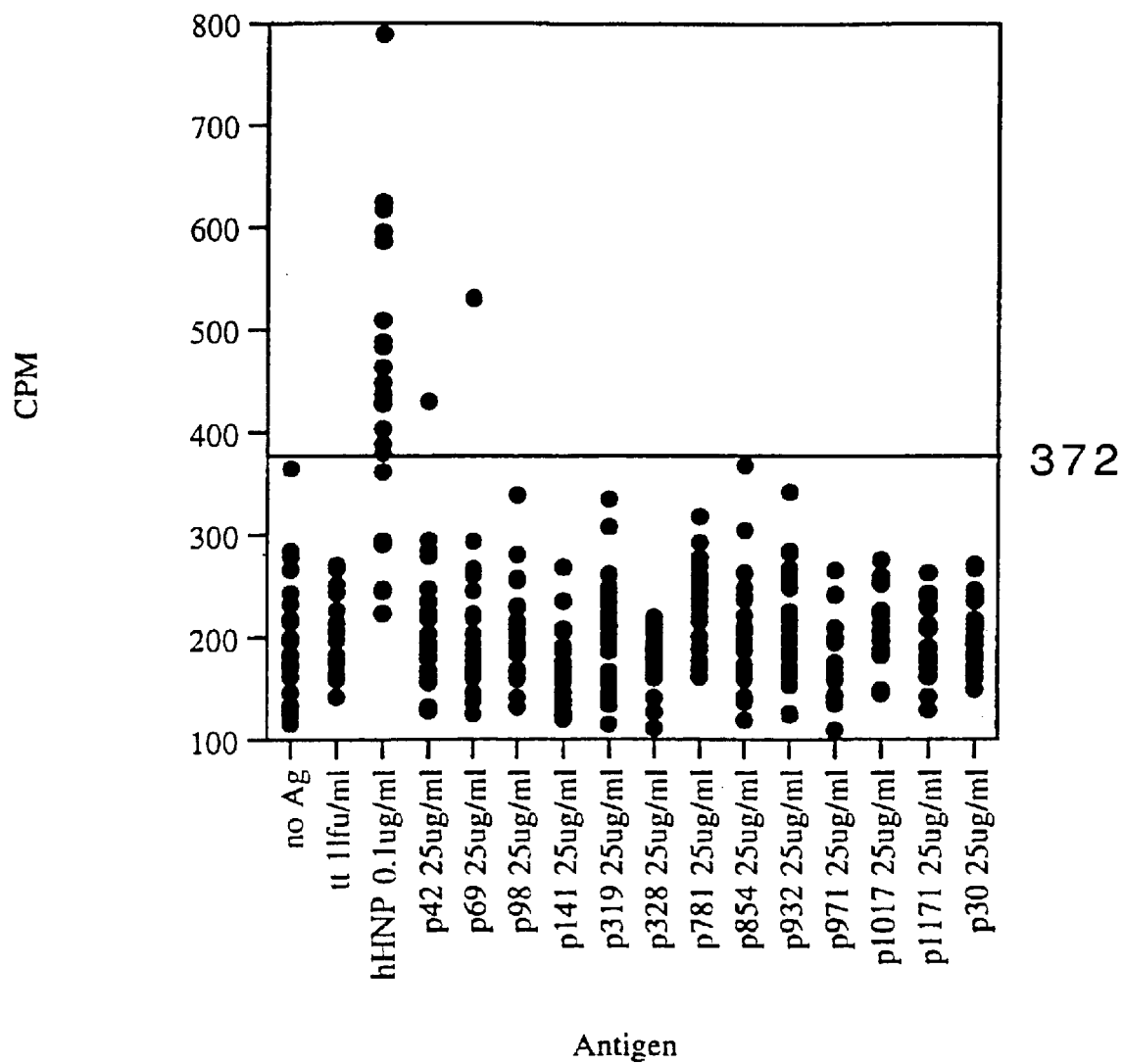

FIG. 4 shows that breast cancer patients have preexistent immunity to HER-2/neu polypeptide. Patient PBMC were evaluated by tritiated thymidine incorporation in 24 well replicates. Responsive wells are scored as greater than the mean and 3 standard deviations (372 cpm) of the control wells. This HER-2/neu positive-stage II breast cancer patient has a significant response to recombinant human HER-2/neu polypeptide. The symbols "p" represent peptides for HER-2/neu protein, "tt" represents tetanus toxoid, and "hHNP" represents recombinant human HER-2/neu polypeptide.

DETAILED DESCRIPTION OF THE INVENTION

Prior to setting forth the invention, it may be helpful to an understanding thereof to set forth definitions of certain terms to be used hereinafter.

HER-2/neu polypeptide—as used herein, refers to a portion of the HER-2/neu protein (the protein also known as p185 or c-erbB2) having the amino acid sequence of SEQ ID NO:2 from lysine, amino acid 676, through valine, amino acid 1255; and may be naturally derived, synthetically produced, genetically engineered, or a functionally equivalent variant thereof, e.g., where one or more amino acids are replaced by other amino acid(s) or non-amino acid(s) which do not substantially affect elicitation or enhancement of an immune response to HER-2/neu protein (e.g., variant stimulates a response by helper T cells or cytotoxic T cells).

Proliferation of T cells—as used herein, includes the multiplication of T cells as well as the stimulation of T cells leading to multiplication, i.e., the initiation of events leading to mitosis and mitosis itself. Methods for detecting proliferation of T cells are discussed below.

As noted above, the present invention is directed toward compounds and compositions to elicit or enhance immunity to the protein product expressed by the HER-2/neu oncogene, including for malignancies in a warm-blooded animal wherein an amplified HER-2/neu gene is associated with the malignancies. Association of an amplified HER-2/neu gene with a malignancy does not require that the protein expression product of the gene be present on the tumor. For example, overexpression of the protein expression product may be involved with initiation of a tumor, but the protein expression may subsequently be lost. A use of the present invention is to elicit or enhance an effective autochthonous immune response to convert a HER-2/neu positive tumor to HER-2/neu negative.

More specifically, the disclosure of the present invention, in one aspect, shows that a polypeptide based on a particular portion (HER-2/neu polypeptide) of the protein expression product of the HER-2/neu gene can be recognized by thymus-dependent lymphocytes (hereinafter "T cells") and, therefore, the autochthonous immune T cell response can be utilized prophylactically or to treat malignancies in which such a protein is or has been overexpressed. The disclosure of the present invention also shows, in another aspect, that nucleic acid molecules directing the expression of such a peptide may be used alone or in a viral vector for immunization.

In general, CD4+ T cell populations are considered to function as helpers/inducers through the release of lymphokines when stimulated by a specific antigen; however, a subset of CD4+ cells can act as cytotoxic T lymphocytes (CTL) Similarly, CD8+ T cells are considered to function by directly lysing antigenic targets; however, under a variety of circumstances they can secrete lymphokines to provide helper or DTH function. Despite the potential of overlapping function, the phenotypic CD4 and CD8 markers are linked to the recognition of peptides bound to class II or class I MHC antigens. The recognition of antigen in the context of class II or class I MHC mandates that CD4+ and CD8+ T cells respond to different antigens or the same antigen presented under different circumstances. The binding of immunogenic peptides to class II MHC antigens most commonly occurs for antigens ingested by antigen presenting cells. Therefore, CD4+ T cells generally recognize antigens that have been external to the tumor cells. By contrast, under normal circumstances, binding of peptides to class I MHC occurs only for proteins present in the cytosol and synthesized by the target itself, proteins in the external environment are excluded. An exception to this is the binding of exogenous peptides with a precise class I binding motif which are present outside the cell in high concentration. Thus, CD4+ and CD8+ T cells have broadly different functions and tend to recognize different antigens as a reflection of where the antigens normally reside.

As disclosed within the present invention, a polypeptide portion of the protein product expressed by the HER-2/neu oncogene is recognized by T cells. Circulating HER-2/neu polypeptide is degraded to peptide fragments. Peptide fragments from the polypeptide bind to major histocompatibility complex (MHC) antigens. By display of a peptide bound to MHC antigen on the cell surface and recognition by host T cells of the combination of peptide plus self MHC antigen, HER-2/neu polypeptide (including that expressed on a malignant cell) will be immunogenic to T cells. The exquisite specificity of the T cell receptor enables individual T cells to discriminate between peptides which differ by a single amino acid residue.

During the immune response to a peptide fragment from the polypeptide, T cells. expressing a T cell receptor with high affinity binding of the peptide-MHC complex will bind to the peptide-MHC complex and thereby become activated and induced to proliferate. In the first encounter with a peptide, small numbers of immune T cells will secrete lymphokines, proliferate and differentiate into effector and memory T cells. The primary immune response will occur in vivo but has been difficult to detect in vitro. Subsequent encounter with the same antigen by the memory T cell will lead to a faster and more intense immune response. The secondary response will occur either in viva or in vitro. The in vitro response is easily gauged by measuring the degree of proliferation, the degree of cytokine production, or the generation of cytolytic activity of the T cell population re-exposed in the antigen. Substantial proliferation of the T cell population in response to a particular antigen is considered to be indicative of prior exposure or priming to the antigen.

The compounds of this invention generally comprise HER-2/neu polypeptides or DNA molecules that direct the expression of such peptides, wherein the DNA molecules may be present in a viral vector. As noted above, the polypeptides of the present invention include variants of the polypeptide of SEQ ID NO:2 from amino acid 676 through amino acid 1255, that retain the ability to stimulate an immune response. Such variants include various structural forms of the native polypeptide. Due to the presence of ionizable amino and carboxyl groups, for example, a HER-2/neu polypeptide may be in the form of an acidic or basic salt, or may be in neutral form. Individual amino acid residues may also be modified by oxidation or reduction.

Variants within the scope of this invention also include polypeptides in which the primary amino acid structure native HER-2/neu polypeptide is modified by forming covalent or aggregative conjugates with other peptides or polypeptides, or chemical moieties such as glycosyl groups, lipids, phosphate, acetyl groups and the like. Covalent derivatives may be prepared, for example, by linking particular functional groups to amino acid side chains or at the N- or C-terminus.

The present invention also includes HER-2/neu polypeptides with or without glycosylation. Polypeptides expressed in yeast or mammalian expression systems may be similar to or slightly different in molecular weight and glycosylation pattern than the native molecules, depending upon the expression system. For instance, expression of DNA encoding polypeptides in bacteria such as E. coli typically provides non-glycosylated molecules. N-glycosylation sites of eukaryotic proteins are characterized by the amino acid triplet Asn-$A_1$-Z, where $A_1$ is any amino acid except Pro, and Z is Ser or Thr. Variants of HER-2/neu polypeptides having inactivated N-glycosylation sites can be produced by techniques known to those of ordinary skill in the art, such as oligonucleotide synthesis and ligation or site-specific mutagenesis techniques, and are within the scope of this invention. Alternatively, N-linked glycosylation sites can be added to a HER-2/neu polypeptide.

The polypeptides of this invention also include variants of the SEQ ID NO:2 polypeptide (i.e., variants of a polypeptide having the amino acid sequence of SEQ ID NO:2 from amino acid 676 through amino acid 1255) that have an amino acid sequence different from this sequence because of one or more deletions, insertions, substitutions or other modifications. In one embodiment, such variants are substantially homologous to the native HER-2/neu polypeptide and retain the ability to stimulate an immune response. "Substantial homology," as used herein, refers to amino acid sequences that may be encoded by DNA sequences that are capable of hybridizing under moderately stringent conditions to a nucleotide sequence complimentary to a naturally occurring DNA sequence encoding the specified polypeptide portion of SEQ ID NO:2 herein (i.e., nucleotides 2026 through 3765 of SEQ ID. NO:1). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC (containing 0.1% SDS). Such hybridizing DNA sequences are also within the scope of this invention. The effect of any such modifications on the ability of a HER-2/neu polypeptide to produce an immune response may be readily determined (e.g., by analyzing the ability of the mutated HER-2/neu polypeptide to induce a T cell response using, for example, the methods described herein).

Generally, amino acid substitutions may be made in a variety of ways to provide other embodiments of variants within the present invention. First, for example, amino acid substitutions may be made conservatively; i.e., a substitute amino acid replaces an amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser. thr; (2) cys, ser, tyr, thr; (3) val, ile, leu, met, ala, phe; (4) lys, arg, his; and (5) phe, tyr, trp, his. An example of a non-conservative change is to replace an amino acid of one group with an amino acid from another group.

Another way to make amino acid substitutions to produce variants of the present invention is to identify and replace amino acids in T cell motifs with potential to bind to class II MHC molecules (for CD4+ T cell response) or class I MHC molecules (for CD8+ T cell response). Peptide segments (of a HER-2/neu polypeptide) with a motif with theoretical potential to bind to class II MHC molecules may be identified by computer analysis. For example, a protein sequence analysis package, T Sites, that incorporates several computer algorithms designed to distinguish potential sites for T cell recognition can be used (Feller and de la Cruz, *Nature* 349:720–721,. 1991). Two searching algorithms are used: (1) the AMPHI algorithm described by Margalit (Feller and de la Cruz, *Nature* 349:720–721, 1991; Margalit et al., *J. Immunol.* 138:2213–2229, 1987) identifies epitope motifs according to alpha-helical periodicity and amphipathicity; (2) the Rothbard and Taylor algorithm identifies epitope motifs according to charge and polarity pattern (Rothbard and Taylor, *EMBO* 7:93–100, 1988). Segments with both motifs are most appropriate for binding to class II MHC molecules. CD8+ T cells recognize peptide bound to class I MHC molecules. Falk, et al. have determined that peptides binding to particular MHC molecules share discernible sequence motifs (Falk et al., *Nature* 351:290–296, 1991). A peptide motif for binding in the groove of HLA-A2.1 has been defined by Edman degradation of peptides stripped from HLA-A2.1 molecules of a cultured cell line (Table 2, from Falk et al., supra). The method identified the typical or average HLA-A2.1 binding peptide as being 9 amino acids in length with dominant anchor residues occurring at positions 2 (L) and 9 (V). Commonly occurring strong binding residues have been identified at positions 2 (M), 4 (E,K), 6 (V), and 8 (K). The identified motif represents the average of many binding peptides.

The HLA-A2.1 Restricted Motif

| | Amino Acid Position | | | | | | | | | Point Assignment |
|---|---|---|---|---|---|---|---|---|---|---|
| | 1 | 2 | 3 | 4 | 5 | 6 | 7 | 8 | 9 | |
| Dominant Binding Anchor Residue | | L | | | | | | | V | +3 |
| Strong Binding Residue | | M | | E K | | V | | K | | +2 |
| Weak Binding Residue | I L F K M Y | | A Y F P M S | G P D T M | I K Y N G V H | I L T | A Y H | E S | L | +1 |

The derived peptide motif as currently defined is not particularly stringent. Some HLA-A2.1 binding peptides do not contain both dominant anchor residues and the amino acids flanking the dominant anchor residues play major roles in allowing or disallowing binding. Not every peptide with the current described binding motif will bind, and some peptides without the motif will bind. However, the current motif is valid enough to allow identification of some peptides capable of binding. Of note, the current HLA-A2.1 motif places 6 amino acids between the dominant anchor amino acids at residues 2 and 9.

Following identification of peptide motifs within a HER-2/neu polypeptide, amino acid substitutions may be made conservatively or non-conservatively. The latter type of substitutions are intended to produce an improved polypeptide that is more potent and/or more broadly cross-reactive MHC polymorphism). An example of a more potent polypeptide is one that binds with higher affinity to the same MHC molecule as natural polypeptide, without affecting recognition by T cells specific for natural polypeptide. An example of a polypeptide with broader cross-reactivity is one that induces more broadly cross-reactive immune responses (i.e., binds to a greater range of MHC molecules) than natural polypeptide. Similarly, one or more amino acids residing between peptide motifs and having a spacer function (e.g., do not interact with a MHC molecule or T cell receptor) may be substituted conservatively or non-conservatively. It will be evident to those of ordinary skill in the art that polypeptides containing one or more amino acid substitutions may be tested for beneficial or adverse immunological interactions by a variety of assays, including those described herein for the ability to stimulate T cell recognition.

Variants within the scope of this invention may also, or alternatively, contain other modifications, including the deletion or addition of amino acids, that have minimal influence on the desired immunological properties of the polypeptide. It will be appreciated by those of ordinary skill in the art that truncated forms or non-native extended forms of a HER-2/neu polypeptide may be used, provided the desired immunological properties are at least roughly equivalent to that of full length, native HER-2/neu polypeptide. Cysteine residues may be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

A HER-2/neu polypeptide may generally be obtained using a genomic or cDNA clone encoding the protein. A genomic sequence that encodes full length HER-2/neu is shown in SEQ ID NO:1, and the deduced amino acid sequence is presented in SEQ ID NO:2. Such clones may be isolated by screening an appropriate expression library for clones that express HER-2/neu protein. The library preparation and screen may generally be performed using methods known to those of ordinary skill in the art, such as methods described in Sambrook et al., *Molecular Cloning: A Laboratory Manual*, Cold Spring Harbor Laboratories, Cold Spring Harbor, N.Y., 1989, which is incorporated herein by reference. Briefly, a bacteriophage expression library may be plated and transferred to filters. The filters may then be incubated with a detection reagent. In the context of this invention, a "detection reagent" is any compound capable of binding to HER-2/neu protein, which may then be detected by any of a variety of means known to those of ordinary skill in the art. Typical detection reagents contain a "binding agent," such as Protein A, Protein G, IgG or a lectin, coupled to a reporter group. Preferred reporter groups include enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenz-thiazoline sulfonic acid. Plaques containing genomic or cDNA sequences that express HER-2/neu protein are isolated and purified by techniques known to those of ordinary skill in the art. Appropriate methods may be found, for example, in Sambrook et al., *Molecular Cloning: A Laboratory Manual*, Cold Spring Harbor Laboratories, Cold Spring Harbor, N.Y., 1989.

Variants of the polypeptide that retain the ability to stimulate an immune response may generally be identified by modifying the sequence in one or more of the aspects described above and assaying the resulting polypeptide for the ability to stimulate an immune response, e.g., a T cell response. For example, such assays may generally be performed by contacting T cells with the modified polypeptide and assaying the response. Naturally occurring variants of the polypeptide may also be isolated by, for example, screening an appropriate cDNA or genomic library with a DNA sequence encoding the polypeptide or a variant thereof.

The above-described sequence modifications may be introduced using standard recombinant techniques or by automated synthesis of the modified polypeptide. For example, mutations can be introduced at particular loci by synthesizing oligonucleotides containing a mutant sequence, flanked by restriction sites enabling ligation to fragments of the native sequence. Following ligation, the resulting reconstructed sequence encodes an analogue having the desired amino acid insertion, substitution, or deletion.

Alternatively, oligonucleotide-directed site-specific mutagenesis procedures can be employed to provide a gene in which particular codons are altered according to the substitution, deletion, or insertion required. Exemplary methods of making the alterations set forth above are disclosed by Walder et al., *Gene* 42:133, 1986; Bauer et al., *Gene* 37:73, 1985; Craik, *BioTechniques*, Jan. 1985, 12–19; Smith et al., *Genetic Engineering: Principles and Methods*, Plenum Press, 1981; and U.S. Pat. Nos. 4,518,584 and 4,737,462.

Mutations in nucleotide sequences constructed for expression of such HER-2/neu polypeptides must, of course, preserve the reading frame of the coding sequences and preferably will not create complementary regions that could hybridize to produce secondary mRNA structures, such as loops or hairpins, which would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed HER-2/neu polypeptide mutants screened for the desired activity.

Not all mutations in a nucleotide sequence which encodes a HER-2/neu polypeptide will be expressed in the final product. For example, nucleotide substitutions may be made to enhance expression, primarily to avoid secondary structure loops in the transcribed mRNA (see, e.g., European Patent Application 75,444A), or to provide codons that are more readily translated by the selected host, such as the well-known *E. coli* preference codons for *E. coli* expression.

The polypeptides of the present invention, both naturally occurring and modified, are preferably produced by recombinant DNA methods. Such methods include inserting a DNA sequence encoding a HER-2/neu polypeptide into a recombinant expression vector and expressing the DNA sequence in a recombinant microbial, mammalian or insect cell expression system under conditions promoting expression. DNA sequences encoding the polypeptides provided by this invention can be assembled from cDNA fragments and short oligonucleotide, linkers, or from a series of oligonucleotides, to provide a synthetic gene which is capable of being inserted in a recombinant expression vector and expressed in a recombinant transcriptional unit.

Recombinant expression vectors contain a DNA sequence encoding a HER-2/neu polypeptide operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation. An origin of replication and a selectable marker to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, in reading frame. DNA sequences encoding HER-2/neu polypeptides which are to be expressed in a microorganism will preferably contain no introns that could prematurely terminate transcription of DNA into mRNA.

Expression vectors for bacterial use may comprise a selectable marker and bacterial origin of replication derived from commercially available plasmids comprising genetic elements of the well known cloning vector pBR322 (ATCC 37017). Such commercial vectors include, for example, pKK223–3 (Pharmacia Fine Chemicals, Uppsala, Sweden) and pGEM1 (Promega Biotec, Madison; Wis., USA). These pBR322 "backbone" sections are combined with an appropriate promoter and the structural sequence to be expressed. E. coli is typically transformed using derivatives of pBR322, a plasmid derived from an E. coli species (Bolivar et al., Gene 2:95, 1977). pBR322 contains genes for ampicillin and tetracycline resistance and thus provides simple means for identifying transformed cells.

Promoters commonly used in recombinant microbial expression vectors include the P-lactamase (penicillinase) and lactose promoter system (Chang et al., Nature 275:615, 1978; and Goeddel et al., Nature 281:544, 1979), the tryptophan (trp) promoter system (Goeddel et al., Nucl. Acids Res. 8:4057, 1980; and European Patent Application 36,776) and the tac promoter (Maniatis, Molecular Cloning: A Laboratory Manual, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in E. coli strain JMB9 (ATCC 37092) and pPLc28, resident in E. coli RRl (ATCC 53082).

Suitable promoter sequences in yeast vectors include the promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., European Patent Application 73,657.

Preferred yeast vectors can be assembled using DNA sequences from pBR322 for selection and replication in E. coli ($Amp^r$ gene and origin of replication) and yeast DNA sequences including a glucose-repressible ADH2 promoter and α-factor secretion leader. The ADH2 promoter has been described by Russell et al. (J. Biol. Chem. 258:2674, 1982) and Beier et al. (Nature 300:724, 1982). The yeast α-factor leader, which directs secretion of heterologous proteins, can be inserted between the promoter and the structural gene to be expressed (see, e.g., Kurjan et al., Cell 30:933, 1982; and Bitter et al., Proc. Natl. Acad. Sci. USA 81:5330, 1984). The leader sequence may be modified to contain, near its 3' end, one or more useful restriction sites to facilitate fusion of the leader sequence to foreign genes. The transcriptional and translational control sequences in expression vectors to be used in transforming vertebrate cells may be provided by viral sources. For example, commonly used promoters and enhancers are derived from polyoma, adenovirus 2, simian virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., Nature 273:113, 1978). Smaller or larger SV40 fragments may also be used, provided the approximately 250 bp sequence extending from the Hind III site toward the Bgl II site located in the viral origin of replication is included. Further, viral genomic promoter, control and/or signal sequences may be utilized, provided such control sequences are compatible with the host cell chosen. Exemplary vectors can be constructed as disclosed by Okayama and Berg, Mol. Cell. Biol. 3:280, 1983.

A useful system for stable high level expression of mammalian receptor cDNAs in C127 murine mammary epithelial cells can be constructed substantially as described by Cosman et al. (Mol. Immunol. 23:935, 1986). A preferred eukaryotic vector for expression of HER-2/neu polypeptide DNA is pDC406 (McMahan et al., EMBO J. 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and OC409, which contain the EBV origin of replication, is CV-l/EBNA (ATCC CRL 10478). The CV-L/EBNA cell line was derived by transfection of the CV-l cell line with a gene encoding Epstein-Barr virus nuclear antigen-I (EBNA-1) and constitutively express EBNA-1 driven from human CMV immediate-early enhancer/promoter.

Transformed host cells are cells which have been transformed or transfected with expression vectors constructed using recombinant DNA techniques and which contain sequences encoding a HER-2/neu polypeptide of the present invention. Transformed host cells may express the desired HER-2/neu polypeptide, but host cells transformed for purposes of cloning or amplifying HER-2/neu DNA do not need to express the HER-2/neu polypeptide. Expressed polypeptides will preferably be secreted into the culture supernatant, depending on the DNA selected, but may also be deposited in the cell membrane.

Suitable host cells for expression of recombinant proteins include prokaryotes, yeast or higher eukaryotic cells under the control of appropriate promoters. Prokaryotes include gram negative or gram positive organisms, for example E. coli or Bacilli. Higher eukaryotic cells include established cell lines of insect or mammalian origin as described below. Cell-free translation systems could also be employed to produce HER-2/neu polypeptides using RNAs derived from DNA constructs. Appropriate cloning and expression vectors for use with bacterial, fungal, yeast, and mammalian cellular hosts are described, for example, by Pouwels et al., Cloning Vectors: A Laboratory Manual, Elsevier, N.Y. 1985.

Prokaryotic expression hosts may be used for expression of HER-2/neu polypeptides that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include E. coli, Bacillus subtilis, Salmonella typhimurium, and various species within the genera Pseudomonas, Streptomyces, and Staphylococcus, although other hosts may also be employed.

Recombinant HER-2/neu polypeptides may also be expressed in yeast hosts, preferably from the *Saccharomyces* species, such as *S. cerevisiae*. Yeast of other genera, such as *Pichia* or *Kluyveromyces* may also be employed. Yeast vectors will generally contain an origin of replication from the 2μ yeast plasmid or an autonomously replicating sequence (ARS), a promoter, DNA encoding the HER-2/neu polypeptide, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and the *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art. An exemplary technique described by Hind et al. (*Proc. Natl. Acad. Sci. USA* 75:1929, 1978), involves selecting for Trp$^+$ transformants in a selective medium consisting of 0.67% yeast nitrogen base, 0.5% casamino acids, 2% glucose, 10 mg/ml adenine and 20 mg/ml uracil. Host strains transformed by vectors comprising the ADH2 promoter may be grown for expression in a rich medium consisting of 1% yeast extract, 2% peptone, and 1% glucose supplemented with 80 mg/ml adenine and 80 mg/ml uracil. Derepression of the ADH2 promoter occurs upon exhaustion of medium glucose. Crude yeast supernatants are harvested by filtration and held at 4° C. prior to further purification.

Various mammalian or insect (e.g., *Spodoptera* or *Trichoplusia*) cell culture systems can also be employed to express recombinant polypeptide. Baculovirus systems for production of heterologous polypeptides in insect cells are reviewed, for example, by Luckow and Summers, *Bio/Technology* 6:47, 1988. Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), COS, NS-1, HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purified HER-2/neu polypeptides may be prepared by culturing suitable host/vector systems to express the recombinant translation products of the DNAs of the present invention, which are then purified from culture media or cell extracts. For example, supernatants from systems which secrete recombinant polypeptide into culture media may be first concentrated using a commercially available protein concentration filter, such as an Amicon or Millipore Pellicon ultrafiltration unit. Following the concentration step, the concentrate may be applied to a suitable purification matrix. For example, a suitable affinity matrix may comprise a counter structure protein (i.e., a protein to which a HER-2/neu polypeptide binds in a specific interaction based on structure) or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying a HER-2/neu.

Affinity chromatography is a preferred method of purifying HER-2/neu polypeptides. For example, monoclonal antibodies against the HER-2/neu polypeptide may also be useful in affinity chromatography purification, by utilizing methods that are well-known in the art.

Finally, one or more reverse-phase high performance liquid chromatography (RP-HPLC) steps employing hydrophobic RP-HPLC media (e.g., silica gel having pendant methyl or other aliphatic groups) may be employed to further purify a HER-2/neu polypeptide composition. Some or all of the foregoing purification steps, in various combinations, can also be employed to provide a homogeneous recombinant polypeptide.

Recombinant HER-2/neu polypeptide produced in bacterial culture is preferably isolated by initial extraction from cell pellets, followed by one or more concentration, salting-out, aqueous ion exchange or size exclusion chromatography steps. High performance liquid chromatography (HPLC) may be employed for final purification steps. Microbial cells employed in expression of recombinant HER-2/neu polypeptide can be disrupted by any convenient method, including freeze-thaw cycling, sonication, mechanical disruption, or use of cell lysing agents.

Fermentation of yeast which express HER-2/neu polypeptide as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reverse-phase HPLC steps for purification of recombinant human GM-CSF on a preparative HPLC column.

Preparations of HER-2/neu polypeptides synthesized in recombinant culture may contain non-HER-2/neu cell components, including proteins, in amounts and of a character which depend upon the purification steps taken to recover the HER-2/neu polypeptide from the culture. These components ordinarily will be of yeast, prokaryotic or non-human eukaryotic origin. Such preparations are typically free of other proteins which may be normally associated with the HER-2/neu protein as it is found in nature in its species of origin.

Automated synthesis provides an alternate method for preparing polypeptides of this invention. For example, any of the commercially available solid-phase techniques may be employed, such as the Merrifield solid phase synthesis method, in which amino acids are sequentially added to a growing amino acid chain. (See Merrifield, *J. Am. Chem. Soc.* 85:2149–2146, 1963.) Equipment for automated synthesis of polypeptides is commercially available from suppliers such as Applied Biosystems, Inc. of Foster City, Calif., and may generally be operated according to the manufacturer's instructions.

Within one aspect of the present invention, use of a HER-2/neu polypeptide (or a DNA molecule that directs the expression of such a peptide) to generate an immune response to the HER-2/neu protein (including that expressed on a malignancy in which a HER-2/neu oncogene is associated) may be detected. Representative examples of such malignancies include breast, ovarian, colon, lung and prostate cancers. An immune response to the HER-2/neu protein, once generated by a HER-2/neu polypeptide, can be long-lived and can be detected long after immunization, regardless of whether the protein is present or absent in the body at the time of testing. An immune response to the HER-2/neu protein generated by reaction to a HER-2/neu polypeptide can be detected by examining for the presence or absence, or enhancement, of specific activation of CD4$^+$ or CD8$^+$ T cells. More specifically, T cells isolated from an immunized individual by routine techniques (such as by Ficoll/Hypaque density gradient centrifugation of peripheral blood lymphocytes) are incubated with HER-2/neu protein. For example, T cells may be incubated in vitro for 2–9 days (typically 4 days) at 37° C. with HER-2/neu protein (typically, 5 µg/ml of whole protein or graded numbers of cells synthesizing HER-2/neu protein). It may be desirable to incubate another aliquot of a T cell sample in the absence of HER-2/neu protein to serve as a control.

Specific activation of CD4$^+$ or CD8$^+$ T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for HER-2/neu protein). For CD4$^+$ T cells, a preferred method for detecting specific T cell activation is the detection of the proliferation of T cells. For CD8$^+$ T cells, a preferred method for detecting specific T cell activation is the detection of the generation of cytolytic activity.

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, Ca$^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to intact p185$^{HER-2/neu}$ protein may be quantified.

By use or expression of a HER-2/neu polypeptide, T cells which recognize the HER-2/neu protein can be proliferated in vivo. For example, immunization with a HER-2/neu peptide (i.e., as a vaccine) can induce continued expansion in the number of T cells necessary for therapeutic attack against a tumor in which the HER-2/neu oncogene is associated. Typically, about 0.01 µg/kg to about 100 mg/kg body weight will be administered by the intradermal, subcutaneous or intravenous route. A preferred dosage is about 1 µg/kg to about 1 mg/kg, with about 5 µg/kg to about 200 µg/kg particularly preferred. It will be evident to those skilled in the art that the number and frequency of administration will be dependent upon the response of the patient. It may be desirable to administer the HER-2/neu polypeptide repetitively. It will be evident to those skilled in this art that more than one HER-2/neu polypeptide may be administered, either simultaneously or sequentially. Preferred peptides for immunization are those that include the amino acid sequence of SEQ ID NO:2 beginning at about the lysine residue at amino acid position 676 and extending to about the valine residue at amino acid position 1255. It will be appreciated by those in the art that the present invention contemplates the use of an intact HER-2/neu polypeptide as well as division of such a polypeptide into a plurality of peptides. Neither intact p185$^{HER-2/neu}$ protein nor a peptide having the amino acid sequence of its entire extracellular domain (i.e., a peptide having an amino acid sequence of SEQ ID NO:2 from amino acid position 1 up to amino acid position 650, plus or minus about one to five positions, and with or without the first 21 amino acid positions) are used alone for immunization.

A HER-2/neu polypeptide (or nucleic acid) is preferably formulated for use in the above methods as a pharmaceutical composition (e.g., vaccine). Pharmaceutical compositions generally comprise one or more polypeptides in combination with a pharmaceutically acceptable carrier, excipient or diluent. Such carriers will be nontoxic to recipients at the dosages and concentrations employed. The use of a HER-2/neu polypeptide in conjunction with chemotherapeutic agents is also contemplated.

In addition to the HER-2/neu polypeptide (which functions as an antigen), it may be desirable to include other components in the vaccine, such as a vehicle for antigen delivery and immunostimulatory substances designed to enhance the protein's immunogenicity. Examples of vehicles for antigen delivery include aluminum salts, water-in-oil emulsions, biodegradable oil vehicles, oil-in-water emulsions, biodegradable microcapsules, and liposomes. Examples of immunostimulatory substances (adjuvants) include N-acetylmuramyl-L-alanine-D-isoglutamine (MDP), lipopoly-saccharides (LPS), glucan, IL-12, GM-CSF, gamma interferon and IL-15. It will be evident to those of ordinary skill in this art that a HER-2/neu polypeptide for a vaccine may be prepared synthetically or be naturally derived.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. A HER-2/neu polypeptide may be encapsulated within the biodegradable microsphere or associated with the surface of the microsphere. For example, in a preferred embodiment, a polypeptide having the amino acid sequence of SEQ ID NO:2 from amino acid 676 through amino acid 1255 is encapsulated within a biodegradable microsphere. In this regard, it is preferable that the microsphere be larger than approximately 25 microns.

Pharmaceutical compositions (including vaccines) may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

Preferably, product is formulated as a lyophilizate using appropriate excipient solutions (e.g., sucrose) as diluents.

As an alternative to the presentation of HER-2/neu polypeptides, the subject invention includes compositions capable of delivering nucleic acid molecules encoding a HER-2/neu polypeptide. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616–627, 1988; Li et al., *Hum. Gene Ther.* 4:403–409, 1993; Vincent et al., *Nat. Genet.* 5:130–134, 1993; and Kolls et al., *Proc. Natl. Acad. Sci. USA* 91:215–219, 1994), pox virus (see U.S. Pat. No. 4,769,330; U.S. Pat. No. 5,017,487; and WO 89/01973)), naked DNA (see WO 90/11092), nucleic acid molecule complexed to a polycationic molecule (see WO 93/03709), and nucleic acid associated with liposomes (see Wang et al., *Proc. Natl. Acad. Sci. USA* 84:7851, 19B7). In certain embodiments, the DNA may be linked to killed or inactivated adenovirus (see Curiel et al., *Hum. Gene Ther.* 3:147–154, 1992; Cotton et al., *Proc. Natl. Acad. Sci. USA* 89:6094, 1992). Other suitable compositions include DNA-ligand (see Wu et al., *J. Biol. Chem.* 264:16985–16987, 1989) and lipid-DNA combinations (see Felgner et al., *Proc. Natl. Acad. Sci. USA* 84:7413–7417, 1989). In addition, the efficiency of naked DNA uptake into cells may be increased by coating the DNA onto biodegradable beads.

In addition to direct in vivo procedures, ex vivo procedures may be used in which cells are removed from an animal, modified, and placed into the same or another animal. It will be evident that one can utilize any of the compositions noted above for introduction of HER-2/neu nucleic acid molecules into tissue cells in an ex vivo context. Protocols for viral, physical and chemical methods of uptake are well known in the art.

Accordingly, the present invention is useful for enhancing or eliciting, in a patient or cell culture, a cellular immune response (e.g., the generation of antigen-specific cytolytic T cells). As used herein, the term "patient" refers to any warm-blooded animal, preferably a human. A patient may be afflicted with cancer, such as breast cancer, or may be normal (i.e., free of detectable disease and infection). A "cell culture" is any preparation of T cells or isolated component cells (including, but not limited to, macrophages, monocytes, B cells and dendritic cells). Such cells may be isolated by any of a variety of techniques well known to those of ordinary skill in the art (such as Ficoll-hypaque density centrifugation). The cells may (but need not) have been isolated from a patient afflicted with a HER-2/neu associated malignancy, and may be reintroduced into a patient after treatment.

The present invention also discloses that HER-2/neu polypeptide, in addition to being immunogenic to T cells, appears to stimulate B-cells to produce antibodies capable of recognizing HER-2/neu polypeptide. Antibodies specific (i.e., which exhibit a binding affinity of about $10^7$ liters/mole or better) for HER-2/neu protein may be found in a variety of body fluids including sera and ascites. Briefly, a body fluid sample is isolated from a warm-blooded animal, such as a human, for whom it is desired to determine whether antibodies specific for HER-2/neu polypeptide are present. The body fluid is incubated with HER-2/neu polypeptide under conditions and for a time sufficient to permit immunecomplexes to form between the polypeptide and antibodies specific for the protein. For example, a body fluid and HER-2/neu polypeptide may be incubated at 4° C. for 24–48 hours. Following the incubation, the reaction mixture is tested for the presence of immunocomplexes. Detection of one or more immunocomplexes formed between HER-2/neu polypeptide and antibodies specific for HER-2/neu polypeptide may be accomplished by a variety of known techniques, such as radioimmunoassays (RIA) and enzyme linked immunosorbent assays (ELISA).

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh, 1970); the "western blot" method of Gordon et al. (U.S. Pat. No. 4,452,901); immunoprecipitation of labeled ligand (Brown et al., *J. Biol. Chem.* 255:4980–4983, 1980); enzyme-linked immunosorbent assays as described by, for example, Raines and Ross (*J. Biol. Chem.* 257:5154–5160, 1982); immunocytochemical techniques, including the use of fluorochromes (Brooks et al., *Clin. Exp. Immunol.* 39: 477, 1980); and neutralization of activity [Bowen-Pope et al., *Proc. Natl. Acad. Sci. USA* 81:2396–2400 (1984)], all of which are hereby incorporated by reference. In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876, all of which are herein incorporated by reference.

For detection purposes, HER-2/neu polypeptide ("antigen") may either be labeled or unlabeled. When unlabeled, the antigen finds use in agglutination assays. In addition, unlabeled antigen can be used in combination with labeled molecules that are reactive with immunocomplexes, or in combination with labeled antibodies (second antibodies) that are reactive with the antibody directed against HER-2/neu polypeptide, such as antibodies specific for immunoglobulin. Alternatively, the antigen can be directly labeled. Where it is labeled, the reporter group can include radioisotopes, fluorophores, enzymes, luminescers, or dye particles. These and other labels are well known in the art and are described, for example, in the following U.S. Pat. Nos. 3,766,162; 3,791,932; 3,817,837; 3,996,345; and 4,233,402.

Typically in an ELISA assay, antigen is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1%–5.0% by weight) of protein, such as BSA, NGS, or BLOTTO. After incubating for a sufficient length of time to allow specific binding to occur, the well is washed to remove unbound protein and then incubated with an anti-species specific immunoglobulin antibody labeled with a reporter group. The reporter group can be chosen from a variety of enzymes, including horseradish peroxidase, beta-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

In one preferred embodiment of this aspect of the present invention, a reporter group is bound to HER-2/neu protein.

The step of detecting immunocomplexes involves removing substantially any unbound HER-2/neu protein and then detecting the presence or absence of the reporter group.

In another preferred embodiment, a reporter group is bound to a second antibody capable of binding to the antibodies specific for HER-2/neu protein. The step of detecting immunocomplexes involves (a) removing substantially any unbound antibody, (b) adding the second antibody, (c) removing substantially any unbound second antibody and then (d) detecting the presence or absence of the reporter group. Where the antibody specific for HER-2/neu protein is derived from a human, the second antibody is an anti-human antibody.

In a third preferred embodiment for detecting immunocomplexes, a reporter group is bound to a molecule capable of binding to the immunocomplexes. The step of detecting involves (a) adding the molecule, (b) removing substantially any unbound molecule, and then (c) detecting the presence or absence of the reporter group. An example of a molecule capable of binding to the immunocomplexes is protein A.

It will be evident to one skilled in the art that a variety of methods for detecting the immunocomplexes may be employed within the present invention. Reporter groups suitable for use in any of the methods include radioisotopes, fluorophores, enzymes, luminescers, and dye particles.

In a related aspect of the present invention, detection of immunocomplexes formed between HER-2/neu polypeptide and antibodies in body fluid which are specific for HER-2/neu polypeptide may be used to monitor the effectiveness of cancer therapy, which involves a HER-2/neu polypeptide, for a malignancy in which the HER-2/neu oncogene is associated. Samples of body fluid taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

The following examples are offered by way of illustration and not by way of limitation.

EXAMPLES

Example 1

EXPRESSION AND PURIFICATION OF RECOMBINANT HUMAN HER-2/NEU POLYPEPTIDE

The human HER-2/neu polypeptide was recovered by the PCR method (e.g., U.S. Pat. Nos. 4,683,195; 4,683,202; 4,800,159) from a plasmid prepared according to Di Fiore et al. (King et al., Science 229:974–976, 1985; Di Fiore et al., Science 237:178–182, 1987) using oligonucleotide primers that additionally introduced a BssHII restriction site and an enterokinase protease site on the 5' end and an EcoRI site on the 3' end. The primer for the 5'-end was 5'-TCTGGCG CGCTGGATGACGATGACAAGAAACGACGGCAGCA GAAGATC-3' (SEQ ID NO:3) while the primer for the 3'-end was 5'-TGAATTCTCGAGTCATTACACTGGCAC GTCCAGACCCAG-3' (SEQ ID NO:4). The resulting 1.8 kb PCR fragment was subcloned into the T-vector from Novagen (Madison, Wis., USA) and the sequence of selected clones was determined on the ABI 373 automated DNA sequencer (Applied Biosystems Inc., Foster City, Calif., USA) using overlapping sequencing primers. PCR fragments with sequence that corresponded to the published DNA sequence for the human HER-2/neu cDNA (SEQ ID NO:1; Coussens et al., Science 230:1132, 1985; Yamamoto et al., Nature 319:230, 1986)were then connected in the correct reading frame via the BssHII site to a modified E. coli thioredoxin reductase. A 6×histidine affinity tag employed in Ni-NTA affinity purification of the expressed fusion protein was incorporated into the thioredoxin reductase fusion partner. This cDNA for the trxA-human HER-2/neu polypeptide fusion protein was subcloned into a modified pET expression vector for expression in E. coli.

While thioredoxin reductase has been reported to stabilize and solubilize other heterologous proteins expressed in E. coli, it did not appear to offer any significant advantage for human HER-2/neu polypeptide expression in E. coli. While a significant proportion of the trxA-HER-2/neu polypeptide fusion protein was soluble, a majority was expressed in inclusion bodies. The fusion protein was also subjected to degradation during expression in E. coli. The presence of the thioredoxin reductase fusion partner may, however, stabilize the protein during purification. The availability of monoclonal antibodies to thioredoxin reductase provides a convenient marker to follow during purification.

For purification of the human HER-2/neu polypeptide with the thioredoxin reductase fusion partner containing the 6×His affinity tag, the E. coli pellet was resuspended with protease inhibitors and lysozyme and sonicated. The inclusion bodies were isolated by centrifugation, and are washed 3× with deoxycholate, the last wash being overnight to remove LPS. The washed inclusion bodies are solubilized in GuHCl for Ni purification. The Ni column was eluted with Imidazole in urea and dialyzed against 10 mM Tris pH8. The recovery of HER-2/neu polypeptide using this protocol was from 80%–95% pure full length protein with the main contaminant being degraded protein. From 500 ml of fermentation, 20 mg were recovered. It was >98% HER-2/neu polypeptide. The techniques used herein are well known to those in the art and have been described, for example, in J. Sambrook et al., *Molecular Cloning: A Laboratory Manual*, 2nd Ed., Cold Spring Harbor Laboratory Press, 1989, Cold Spring Harbor, N.Y., USA.

Example 2

DENDRITIC CELLS CAN PRIME HUMAN HER-2/NEU POLYPEPTIDE

A. Generation of DC Cultures From Bone Marrow

DC cultures were generated from CD34+ hematopoietic progenitor cells (HPC). CD34+ cells were purified from bone marrow of normal donors using the cell separation system Ceprate LC Kit (CellPro, Bothell, Wash., USA). Purity of recovered CD34+ cells was determined by flow cytometric analysis to be 80% to 95%. CD34+ cells were cultured in serum-free medium (X-VIVO 10, Biowhittaker, Inc., Walkersville, Md., USA) supplemented with L-glutamine (584 $\mu$g/l), penicillin (10 IU/ml), streptomycin (100 $\mu$g/ml), 100 ng/ml human rGM-CSF and 50 ng/ml human rIL-6 (Immunex, Seattle, Wash., USA). After 0 to 17 days of culture time, cells were harvested and used for phenotyping and T cell stimulation assays. GM-CSF alone and in combination with IL-4 or TNFa have been described to induce the in vitro growth of DC. In experiments using KLH and OVA as antigens to prime naive T cells, GM-CSF plus IL-6 consistently gave a comparable total stimulation, but with a lower background and thus a higher stimulation index as compared to GM-CSF plus IL-4 or TNFa.

B. T Cell Priming Assay

Bone marrow derived CD34+ HPC cultured in serum-free medium containing GM-CSF and IL-6 were used as APC after a culture period of 0–17 days. Priming ability of DC was determined by culturing them with autologous, naive T lymphocytes in the presence or absence of the protein antigen recombinant human HER-2/neu polypeptide (hHNP) (10 µg/ml). CD4+ T lymphocytes were isolated from peripheral blood mononuclear cells by positive selection using immunoaffinity columns (CellPro, Inc., Bothell Wash., USA). CD4+ CD45RA+ (naive) T lymphocytes were selected from CD4+ T lymphocytes using an anti-CD45RA mAb directly conjugated to FITC (Immunotech, Westbrook, Me., USA) by flow cytometric sorting. The CD4+ CD45RA+ T cells obtained were 99% pure. DC cultures were plated into 96-well round-bottomed plates (Corning, Corning, N.Y., USA) at various concentrations and incubated for 16–18 hours with hHNP 10 µg/ml final concentration. Antigen-pulsed DC were irradiated (10 Gy), and autologous CD4+ CD45RA+ T lymphocytes were added ($5 \times 10^4$/well). Proliferative response of T cells was measured by the uptake of ($^3$H) thymidine (1 µCi/well) added on day 6 for 16–18 hours. Proliferation assays were performed in serum-free and cytokine-free medium. The results are shown in FIG. 1. FIG. 2 shows the results of testing CD4+ T cells, from a normal donor, for responses to HHNP. Similar data was obtained with T cells from nine out of ten normal individuals.

Example 3

ASSAY FOR DETECTING LOW FREQUENCY LYMPHOCYTE PRECURSORS

Three assays can be used for the detection of CD4$^+$ responses: a standard proliferation assay, a screening method for low frequency events, and a limiting dilution assay (LDA). Conventional proliferative assays are capable of readily detecting primed responses. The proliferative response stimulation index provides a rough correlation with precursor frequency of antigen-reactive T cells. Any specific proliferative response detected from PBL is considered to be a primed response.

To provide a more quantitative interpretation of CD4$^+$ T cell responses, the assay system developed for detecting low lymphocyte precursor frequency responses (described below) is used. This assay is simple and cost-effective. In circumstances in which more precision is needed, the precursor frequency is validated by limiting dilution assays (Bishop and Orosz, *Transplantation* 47:671–677, 1989).

Responses greater than detected in normal individuals are defined as a primed response and imply existent immunity. Low responses, detectable only by LDA conditions are considered to be unprimed responses. An absent response by LDA or a response lower than that defined by the normal population analysis is considered to be tolerance/anergy.

In general, primed CD4$^+$ T cell responses can be detected in conventional proliferative assays, whereas unprimed responses are not detectable in the same assays. Detection of small numbers of unprimed T cells is limited by confounding background thymidine uptake including the autologous mixed lymphocyte response (AMLR) to self MHC antigen plus responses to processed self serum proteins and exogenously added serum proteins.

To elicit and detect unprimed T cells, an assay system for low frequency responses based on Poisson sampling statistics was used (In: *Pinnacles*, Chiron Corporation, 1:1–2, 1991). This type of analysis applies specifically to low frequency events in that, if the precursor frequency is less than the number of cells in one replicate culture, many replicates are required to detect a statistically significant number of positives. Theoretically, the analysis will correct for autologous responses by setting up a known positive control (such as PHA or tetanus toxoid) and known negative control (no antigen) and evaluating all data points from lowest to highest irrespective of the experimental group to which they belong. A cutoff value is calculated based on the equation cutoff=M+(F+SD), where M+arithmetic mean, F=3.29, a factor from tables of standardized normal distribution chosen so not more than 0.1% of the "true negatives" of a normally distributed background will be above the cutoff, and SD=standard deviation. In this screening assay, wells above the cutoff are considered true positives that potentially contain a lymphocyte that is specifically proliferating to the antigen of interest. Although estimations of lymphocyte precursor frequency is possible using this method, precise determination requires formal LDA analysis.

Example 4

HER-2/NEU POLYPEPTIDE BASED VACCINE ELICITS IMMUNITY TO HER-2/NEU PROTEIN

A. Animals

Rats used in this study were Fischer strain 344 (CDF (F-344)/CrlBR) (Charles River Laboratories, Portage Mich.). Animals were maintained at the University of Washington Animal facilities under specific pathogen free conditions and routinely used for experimental studies between 3 and 4 months of age.

B. Immunization

Fischer rats were immunized with recombinant rat HER-2/neu polypeptide (rHNP) in a variety of adjuvants (MPL, Vaccel; Ribi, Bozeman, Mont., USA). Animals received 50 µg of rHNP mixed with adjuvant subcutaneously. Twenty days later the animals were boosted with a second immunization of 50 µg of rHNP administered in the same fashion. Twenty days after the booster immunization animals were tested for the presence of antibodies directed against rat HER-2/neu protein (neu).

C. Cell Lines

Two cell lines were used as a source of neu proteins. SKBR3, a human breast cancer cell line that is a marked overexpressor of HER-2/neu (American Type Culture Collection, Rockville, Md.), was maintained in culture in 10% fetal bovine serum (FBS) (Gemini Bioproducts, Inc., Calabasas, Calif.) and RPMI. DHFR-G8, an NIH/3T3 cell line cotransfected with cneu-p and pSV2-DHFR (American Type Culture Collection, Rockville, Md.), was used as a source of non-transforming rat neu protein (Bernards et al., *Proc. Natl. Acad. Sci.* USA 84:6854–6858, 1987). This cell line was maintained in 10% FBS and Dulbecco's modified Eagle's medium with 4.5 g/L glucose. DHFR-G8 cells were passaged through the same medium supplemented with 0.3 µM methotrexate at every third passage to maintain the neu transfectant.

D. Preparation of Cell Lysates

Lysates of both SKBR3 and DHFR-G8 were prepared and used as a source of neu protein. Briefly, a lysis buffer consisting of tris base, sodium chloride and Triton-X (1%) pH 7.5 was prepared. Protease inhibitors were added; aprotinin (1 µg/ml), benzamidine (1 mM) and PMSF (1 mM). 1 ml of the lysis buffer was used to suspend $10^7$ cells. The cells were vortexed for 15 seconds every 10 minutes for an hour until disrupted. All procedures were performed on ice in a 4° C. cold room. After disruption the cells were microfuged at 4° C. for 20 minutes. Supernatant was removed from cell debris and stored in small aliquots at −70° C. until used.

Presence of human and rat neu in the lysates was documented by Western blot analysis.

E. ELISA for Rat neu Antibody Responses 96 well Immulon 4 plates (Baxter SP, Redmond, Wash.: Dynatech Laboratories) were incubated overnight at 4° C. with a rat neu specific monoclonal antibody (Oncogene Science), 7.16.4, at a concentration of 10 $\mu$/ml diluted in carbonate buffer (equimolar concentrations of $Na_2CO_3$ and $NaHCO_3$ pH 9.6). After incubation, all wells were blocked with PBS-1% BSA (Sigma Chemical, St. Louis, Mo., USA), 100 $\mu$l/well for 3 hours at room temperature. The plate was washed with PBS-0.5% Tween and lysates of DHFRG8, a murine cell line transfected with rat neu DNA (American Type Culture Collection, Rockville, Md., USA); a source of rat neu protein, were added to alternating rows. The plate was incubated overnight at 4° C. The plate was then washed with PBS-0.5% Tween and experimental sera was added at the following dilutions: 1:25 to 1:200. The sera was diluted in PBS-1% BSA-1% FBS-25 $\mu$g/ml mouse IgG-0.01% $NaN_3$ and then serially into PBS-1% BSA. 50 $\mu$l of diluted sera was added/well and incubated 1 hour at room temperature. Each experimental sera was added to a well with rat neu and a well without rat neu. Sheep anti-rat Ig F(ab')$_2$ horseradish peroxidase (HRP) was added to the wells at a 1:5000 dilution in PBS-1% BSA and incubated for 45 minutes at room temperature (Amersham Co., Arlington Heights, Ill., USA). Following the final wash, TMB (Kirkegaard and Perry Laboratories, Gaithersburg, Md.) developing reagent was added. Color reaction was read at an optical density of 450 nm. The OD of each serum dilution was calculated as the OD of the rat neu coated wells minus the OD of the PBS-1% BSA coated wells. Sera from animals immunized with the adjuvants alone and an animal immunized with hHNP (foreign protein) were also evaluated in a similar manner. The results are shown in FIG. 3.

F. T Cell Proliferation Assays

For analysis of HER-2/neu polypeptide specific responses: Fresh spleen or lymph node cells are harvested by mechanical disruption and passage through wire mesh and washed. $2 \times 10^5$ spleen cells/well and $1 \times 10^5$ lymph node cells/well are plated into 96-well round bottom microtiter plates (Corning, Corning, N.Y.) with 6 replicates per experimental group. The media consists of EHAA 120 (Biofluids) with L-glutamine, penicillin/streptomycin, 2-mercaptoethanol, and 5% FBS. Cells are incubated with polypeptides. After 4 days, wells are pulsed with 1 $\mu$Ci of [$^3$H]thymidine for 6–8 hours and counted. Data is expressed as a stimulation index (SI) which is defined as the mean of the experimental wells divided by the mean of the control wells (no antigen). For analysis of HER-2/neu protein specific responses: Spleen or lymph node cells are cultured for 3 in vitro stimulations. At the time of analysis $1 \times 10^5$ cultured spleen or lymph node T cells are plated into 96 well microtiter plates as described above. Cells are incubated with 1 $\mu$g/ml immunoaffinity column purified rat neu (from DHFR-G8 cells as the source of rat neu). After 4 days, wells were pulsed with 1 $\mu$Ci of [$^3$H]thymidine for 6–8 hours and counted. Data is expressed as a stimulation index which is defined as the mean of the experimental wells divided by the mean of the control wells (no antigen).

Example 5

PRIMED RESPONSES TO HUMAN HER-2/NEU POLYPEPTIDE CAN BE DETECTED IN PATIENTS WITH BREAST CANCER

Heparinized blood was obtained from a patient with stage II HER-2/neu overexpressing breast cancer. Peripheral blood mononuclear cells (PBMC) were separated by Ficoll Hypaque density centrifugation. PBMC were plated at a concentration of $2 \times 10^5$/well into 96-well round-bottomed plates (Corning, Corning, N.Y., USA). 24 well replicates were performed for each experimental group. Antigens consisting of HER-2/neu derived peptides (15–20 amino acids in length with number of first amino acid in sequence listed) 25 $\mu$g/ml, human HER-2/neu polypeptide (hHNP) 1 $\mu$g/ml, tetanus toxoid 1 $\mu$g/ml, and p30 a peptide derived from tetanus 25 $\mu$g/ml were added to each 24 well replicate. The assay was performed in media containing 10% human sera. Proliferative response of T cells was measured by the uptake of ($^3$H) thymidine (1 $\mu$Ci/well) added on day 4 for 10 hours. Positive wells, antigen reactive wells, were scored as positive if the cpm was greater than the mean and 3 standard deviations of the no antigen wells. The results are shown in FIG. 4. This stage II breast cancer patient has a significant response to recombinant hHNP.

All publications and patent applications mentioned in this specification are herein incorporated by reference to the same extent as if each individual publication or patent application was specifically and individually incorporated by reference.

From the foregoing, it will be evident that, although specific embodiments of the invention have been described herein for purposes of illustration, various modifications may be made without deviating from the spirit and scope of the invention.

What is claimed is:

1. A method for eliciting or enhancing an immune response to HER-2/neu protein, comprising transfecting antigen presenting cells of a warm-blooded animal ex vivo with a nucleic acid molecule and subsequently delivering the transfected cells to the animal in an amount effective to elicit or enhance said response, wherein the nucleic acid molecule directs the expression of a polypeptide encoded by a DNA sequence selected from:

(a) nucleotides 2026 through 3765 of SEQ ID NO:1, and
   (b) DNA sequences that hybridize to a nucleotide sequence complementary to nucleotides 2026 through 3765 of SEQ ID NO:1 under moderately stringent conditions, wherein the DNA sequence encodes a polypeptide that produces an immune response to HER-2/neu protein, and wherein the hybridization conditions comprise prewashing in a solution of 5×SSC, 0.5% SDS, 1.0 mM EDTA (pH 8.0); hybridization at 50° to 65° C. in 5×SSC overnight, followed by washing twice at 65° C. for 20 minutes with each of 2×, 0.5× and 0.2×SSC containing 0.1% SDS, with the proviso that the polypeptide of (b) is not intact HER-2/neu protein.

2. A method for eliciting or enhancing an immune response to HER-2/neu protein, comprising infecting antigen presenting cells of a warm-blooded animal ex vivo with a viral vector and subsequently delivering the infected cells to the animal in an amount effective to elicit or enhance said response, wherein the viral vector directs the expression of a polypeptide encoded by a DNA sequence selected from:

(a) nucleotides 2026 through 3765 of SEQ ID NO:1, and
   (b) DNA sequences that hybridize to a nucleotide sequence complementary to nucleotides 2026 through 3765 of SEQ ID NO:1 under moderately stringent conditions, wherein the DNA sequence encodes a polypeptide that produces an immune response to HER-2/neu protein, and wherein the hybridization conditions comprise prewashing in a solution of 5×SSC, 0.5% SDS, 1.0 mM EDTA (pH 8.0), hybridization at 50° to 65° C. in 5×SSC overnight; followed by washing twice at 65° C. for 20 minutes with each of 2×, 0.5× and 0.2×SSC containing 0.1% SDS, with the proviso that the polypeptide of (b) is not intact HER-2/neu protein.

3. The method of claims 1 or 2 wherein the polypeptide has the amino acid sequence of SEQ ID NO:2 from amino acid 676 through amino acid 1255.

* * * * *

UNITED STATES PATENT AND TRADEMARK OFFICE
CERTIFICATE OF CORRECTION

PATENT NO. : 6,953,573 B1
DATED : October 11, 2005
INVENTOR(S) : Martin A. Cheever et al.

It is certified that error appears in the above-identified patent and that said Letters Patent is hereby corrected as shown below:

Column 1,
Line 21, before the "Technical Field", please insert the following:
-- This invention was made with government support under grant number R01 CA49850 awarded by the National Institutes of Health. The government may have certain rights in the invention. --.

Signed and Sealed this

Twentieth Day of December, 2005

JON W. DUDAS
*Director of the United States Patent and Trademark Office*

UNITED STATES PATENT AND TRADEMARK OFFICE
CERTIFICATE OF CORRECTION

PATENT NO.   : 6,953,573 B1
DATED        : October 11, 2005
INVENTOR(S)  : Martin A. Cheever et al.

It is certified that error appears in the above-identified patent and that said Letters Patent is hereby corrected as shown below:

Title page,
Item [56], References Cited, OTHER PUBLICATIONS,
"Mori et al., "In Vitro and in vivo Release of Soluble erbB-2 Protein from Human Carcinoma Cells," *Japanese Journal of Cancer Research 81:* 489-494, 1900."
Should read as:
-- Mori et al., "In Vitro and in vivo Release of Soluble erbB-2 Protein from Human Carcinoma Cells," *Japanese Journal of Cancer Research 81:* 489-494, 1990. --.

Signed and Sealed this

Seventh Day of February, 2006

JON W. DUDAS
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3768 base pairs
      (B) TYPE: nucleic acid
      (C) STRANDEDNESS: single
      (D) TOPOLOGY: linear (ix) FEATURE:
    (A) NAME/KEY: CDS
    (B) LOCATION: 1..3765

(xi) SEQUENCE DESCRIPTION: SEQ ID NO:1:

```
ATG GAG CTG GCG GCC TTG TGC CGC TGG GGG CTC CTC CTC GCC CTC TTG        48
Met Glu Leu Ala Ala Leu Cys Arg Trp Gly Leu Leu Leu Ala Leu Leu
1               5                   10                  15

CCC CCC GGA GCC GCG AGC ACC CAA GTG TGC ACC GGC ACA GAC ATG AAG        96
Pro Pro Gly Ala Ala Ser Thr Gln Val Cys Thr Gly Thr Asp Met Lys
            20                  25                  30

CTG CGG CTC CCT GCC AGT CCC GAG ACC CAC CTG GAC ATG CTC CGC CAC       144
Leu Arg Leu Pro Ala Ser Pro Glu Thr His Leu Asp Met Leu Arg His
        35                  40                  45

CTC TAC CAG GGC TGC CAG GTG GTG CAG GGA AAC CTG GAA CTC ACC TAC       192
Leu Tyr Gln Gly Cys Gln Val Val Gln Gly Asn Leu Glu Leu Thr Tyr
50                  55                  60

CTG CCC ACC AAT GCC AGC CTG TCC TTC CTG CAG GAT ATC CAG GAG GTG       240
Leu Pro Thr Asn Ala Ser Leu Ser Phe Leu Gln Asp Ile Gln Glu Val
65                  70                  75                  80

CAG GGC TAC GTG CTC ATC GCT CAC AAC CAA GTG AGG CAG GTC CCA CTG       288
Gln Gly Tyr Val Leu Ile Ala His Asn Gln Val Arg Gln Val Pro Leu
                85                  90                  95

CAG AGG CTG CGG ATT GTG CGA GGC ACC CAG CTC TTT GAG GAC AAC TAT       336
Gln Arg Leu Arg Ile Val Arg Gly Thr Gln Leu Phe Glu Asp Asn Tyr
            100                 105                 110

GCC CTG GCC GTG CTA GAC AAT GGA GAC CCG CTG AAC AAT ACC ACC CCT       384
Ala Leu Ala Val Leu Asp Asn Gly Asp Pro Leu Asn Asn Thr Thr Pro
        115                 120                 125

GTC ACA GGG GCC TCC CCA GGA GGC CTG CGG GAG CTG CAG CTT CGA AGC       432
Val Thr Gly Ala Ser Pro Gly Gly Leu Arg Glu Leu Gln Leu Arg Ser
130                 135                 140

CTC ACA GAG ATC TTG AAA GGA GGG GTC TTG ATC CAG CGG AAC CCC CAG       480
Leu Thr Glu Ile Leu Lys Gly Gly Val Leu Ile Gln Arg Asn Pro Gln
145                 150                 155                 160

CTC TGC TAC CAG GAC ACG ATT TTG TGG AAG GAC ATC TTC CAC AAG AAC       528
Leu Cys Tyr Gln Asp Thr Ile Leu Trp Lys Asp Ile Phe His Lys Asn
                165                 170                 175

AAC CAG CTG GCT CTC ACA CTG ATA GAC ACC AAC CGC TCT CGG GCC TGC       576
Asn Gln Leu Ala Leu Thr Leu Ile Asp Thr Asn Arg Ser Arg Ala Cys
            180                 185                 190

CAC CCC TGT TCT CCG ATG TGT AAG GGC TCC CGC TGC TGG GGA GAG AGT       624
His Pro Cys Ser Pro Met Cys Lys Gly Ser Arg Cys Trp Gly Glu Ser
        195                 200                 205

TCT GAG GAT TGT CAG AGC CTG ACG CGC ACT GTC TGT GCC GGT GGC TGT       672
Ser Glu Asp Cys Gln Ser Leu Thr Arg Thr Val Cys Ala Gly Gly Cys
210                 215                 220

GCC CGC TGC AAG GGG CCA CTG CCC ACT GAC TGC TGC CAT GAG CAG TGT       720
Ala Arg Cys Lys Gly Pro Leu Pro Thr Asp Cys Cys His Glu Gln Cys
225                 230                 235                 240

GCT GCC GGC TGC ACG GGC CCC AAG CAC TCT GAC TGC CTG GCC TGC CTC       768
Ala Ala Gly Cys Thr Gly Pro Lys His Ser Asp Cys Leu Ala Cys Leu
                245                 250                 255

CAC TTC AAC CAC AGT GGC ATC TGT GAG CTG CAC TGC CCA GCC CTG GTC       816
His Phe Asn His Ser Gly Ile Cys Glu Leu His Cys Pro Ala Leu Val
            260                 265                 270

ACC TAC AAC ACA GAC ACG TTT GAG TCC ATG CCC AAT CCC GAG GGC CGG       864
Thr Tyr Asn Thr Asp Thr Phe Glu Ser Met Pro Asn Pro Glu Gly Arg
        275                 280                 285
```

-continued

| | |
|---|---|
| TAT ACA TTC GGC GCC AGC TGT GTG ACT GCC TGT CCC TAC AAC TAC CTT<br>Tyr Thr Phe Gly Ala Ser Cys Val Thr Ala Cys Pro Tyr Asn Tyr Leu<br>290                        295                     300 | 912 |
| TCT ACG GAC GTG GGA TCC TGC ACC CTC GTC TGC CCC CTG CAC AAC CAA<br>Ser Thr Asp Val Gly Ser Cys Thr Leu Val Cys Pro Leu His Asn Gln<br>305                     310                     315                 320 | 960 |
| GAG GTG ACA GCA GAG GAT GGA ACA CAG CGG TGT GAG AAG TGC AGC AAG<br>Glu Val Thr Ala Glu Asp Gly Thr Gln Arg Cys Glu Lys Cys Ser Lys<br>                   325                     330                     335 | 1008 |
| CCC TGT GCC CGA GTG TGC TAT GGT CTG GGC ATG GAG CAC TTG CGA GAG<br>Pro Cys Ala Arg Val Cys Tyr Gly Leu Gly Met Glu His Leu Arg Glu<br>             340                     345                     350 | 1056 |
| GTG AGG GCA GTT ACC AGT GCC AAT ATC CAG GAG TTT GCT GGC TGC AAG<br>Val Arg Ala Val Thr Ser Ala Asn Ile Gln Glu Phe Ala Gly Cys Lys<br>       355                     360                     365 | 1104 |
| AAG ATC TTT GGG AGC CTG GCA TTT CTG CCG GAG AGC TTT GAT GGG GAC<br>Lys Ile Phe Gly Ser Leu Ala Phe Leu Pro Glu Ser Phe Asp Gly Asp<br>370                     375                     380 | 1152 |
| CCA GCC TCC AAC ACT GCC CCG CTC CAG CCA GAG CAG CTC CAA GTG TTT<br>Pro Ala Ser Asn Thr Ala Pro Leu Gln Pro Glu Gln Leu Gln Val Phe<br>385                     390                     395                 400 | 1200 |
| GAG ACT CTG GAA GAG ATC ACA GGT TAC CTA TAC ATC TCA GCA TGG CCG<br>Glu Thr Leu Glu Glu Ile Thr Gly Tyr Leu Tyr Ile Ser Ala Trp Pro<br>                     405                     410                     415 | 1248 |
| GAC AGC CTG CCT GAC CTC AGC GTC TTC CAG AAC CTG CAA GTA ATC CGG<br>Asp Ser Leu Pro Asp Leu Ser Val Phe Gln Asn Leu Gln Val Ile Arg<br>             420                     425                     430 | 1296 |
| GGA CGA ATT CTG CAC AAT GGC GCC TAC TCG CTG ACC CTG CAA GGG CTG<br>Gly Arg Ile Leu His Asn Gly Ala Tyr Ser Leu Thr Leu Gln Gly Leu<br>       435                     440                     445 | 1344 |
| GGC ATC AGC TGG CTG GGG CTG CGC TCA CTG AGG GAA CTG GGC AGT GGA<br>Gly Ile Ser Trp Leu Gly Leu Arg Ser Leu Arg Glu Leu Gly Ser Gly<br>450                     455                     460 | 1392 |
| CTG GCC CTC ATC CAC CAT AAC ACC CAC CTC TGC TTC GTG CAC ACG GTG<br>Leu Ala Leu Ile His His Asn Thr His Leu Cys Phe Val His Thr Val<br>465                     470                     475                 480 | 1440 |
| CCC TGG GAC CAG CTC TTT CGG AAC CCG CAC CAA GCT CTG CTC CAC ACT<br>Pro Trp Asp Gln Leu Phe Arg Asn Pro His Gln Ala Leu Leu His Thr<br>                     485                     490                     495 | 1488 |
| GCC AAC CGG CCA GAG GAC GAG TGT GTG GGC GAG GGC CTG GCC TGC CAC<br>Ala Asn Arg Pro Glu Asp Glu Cys Val Gly Glu Gly Leu Ala Cys His<br>             500                     505                     510 | 1536 |
| CAG CTG TGC GCC CGA GGG CAC TGC TGG GGT CCA GGG CCC ACC CAG TGT<br>Gln Leu Cys Ala Arg Gly His Cys Trp Gly Pro Gly Pro Thr Gln Cys<br>       515                     520                     525 | 1584 |
| GTC AAC TGC AGC CAG TTC CTT CGG GGC CAG GAG TGC GTG GAG GAA TGC<br>Val Asn Cys Ser Gln Phe Leu Arg Gly Gln Glu Cys Val Glu Glu Cys<br>530                     535                     540 | 1632 |
| CGA GTA CTG CAG GGG CTC CCC AGG GAG TAT GTG AAT GCC AGG CAC TGT<br>Arg Val Leu Gln Gly Leu Pro Arg Glu Tyr Val Asn Ala Arg His Cys<br>545                     550                     555                 560 | 1680 |
| TTG CCG TGC CAC CCT GAG TGT CAG CCC CAG AAT GGC TCA GTG ACC TGT<br>Leu Pro Cys His Pro Glu Cys Gln Pro Gln Asn Gly Ser Val Thr Cys<br>                     565                     570                     575 | 1728 |
| TTT GGA CCG GAG GCT GAC CAG TGT GTG GCC TGT GCC CAC TAT AAG GAC<br>Phe Gly Pro Glu Ala Asp Gln Cys Val Ala Cys Ala His Tyr Lys Asp<br>             580                     585                     590 | 1776 |
| CCT CCC TTC TGC GTG GCC CGC TGC CCC AGC GGT GTG AAA CCT GAC CTC<br>Pro Pro Phe Cys Val Ala Arg Cys Pro Ser Gly Val Lys Pro Asp Leu<br>       595                     600                     605 | 1824 |

```
TCC TAC ATG CCC ATC TGG AAG TTT CCA GAT GAG GAG GGC GCA TGC CAG       1872
Ser Tyr Met Pro Ile Trp Lys Phe Pro Asp Glu Glu Gly Ala Cys Gln
    610             615             620

CCT TGC CCC ATC AAC TGC ACC CAC TCC TGT GTG GAC CTG GAT GAC AAG       1920
Pro Cys Pro Ile Asn Cys Thr His Ser Cys Val Asp Leu Asp Asp Lys
625             630             635             640

GGC TGC CCC GCC GAG CAG AGA GCC AGC CCT CTG ACG TCC ATC ATC TCT       1968
Gly Cys Pro Ala Glu Gln Arg Ala Ser Pro Leu Thr Ser Ile Ile Ser
                645             650             655

GCG GTG GTT GGC ATT CTG CTG GTC GTG GTC TTG GGG GTG GTC TTT GGG       2016
Ala Val Val Gly Ile Leu Leu Val Val Val Leu Gly Val Val Phe Gly
660             665             670

ATC CTC ATC AAG CGA CGG CAG CAG AAG ATC CGG AAG TAC ACG ATG CGG       2064
Ile Leu Ile Lys Arg Arg Gln Gln Lys Ile Arg Lys Tyr Thr Met Arg
            675             680             685

AGA CTG CTG CAG GAA ACG GAG CTG GTG GAG CCG CTG ACA CCT AGC GGA       2112
Arg Leu Leu Gln Glu Thr Glu Leu Val Glu Pro Leu Thr Pro Ser Gly
    690             695             700

GCG ATG CCC AAC CAG GCG CAG ATG CGG ATC CTG AAA GAG ACG GAG CTG       2160
Ala Met Pro Asn Gln Ala Gln Met Arg Ile Leu Lys Glu Thr Glu Leu
705             710             715             720

AGG AAG GTG AAG GTG CTT GGA TCT GGC GCT TTT GGC ACA GTC TAC AAG       2208
Arg Lys Val Lys Val Leu Gly Ser Gly Ala Phe Gly Thr Val Tyr Lys
                725             730             735

GGC ATC TGG ATC CCT GAT GGG GAG AAT GTG AAA ATT CCA GTG GCC ATC       2256
Gly Ile Trp Ile Pro Asp Gly Glu Asn Val Lys Ile Pro Val Ala Ile
            740             745             750

AAA GTG TTG AGG GAA AAC ACA TCC CCC AAA GCC AAC AAA GAA ATC TTA       2304
Lys Val Leu Arg Glu Asn Thr Ser Pro Lys Ala Asn Lys Glu Ile Leu
    755             760             765

GAC GAA GCA TAC GTG ATG GCT GGT GTG GGC TCC CCA TAT GTC TCC CGC       2352
Asp Glu Ala Tyr Val Met Ala Gly Val Gly Ser Pro Tyr Val Ser Arg
770             775             780

CTT CTG GGC ATC TGC CTG ACA TCC ACG GTG CAG CTG GTG ACA CAG CTT       2400
Leu Leu Gly Ile Cys Leu Thr Ser Thr Val Gln Leu Val Thr Gln Leu
785             790             795             800

ATG CCC TAT GGC TGC CTC TTA GAC CAT GTC CGG GAA AAC CGC GGA CGC       2448
Met Pro Tyr Gly Cys Leu Leu Asp His Val Arg Glu Asn Arg Gly Arg
                805             810             815

CTG GGC TCC CAG GAC CTG CTG AAC TGG TGT ATG CAG ATT GCC AAG GGG       2496
Leu Gly Ser Gln Asp Leu Leu Asn Trp Cys Met Gln Ile Ala Lys Gly
            820             825             830

ATG AGC TAC CTG GAG GAT GTG CGG CTC GTA CAC AGG GAC TTG GCC GCT       2544
Met Ser Tyr Leu Glu Asp Val Arg Leu Val His Arg Asp Leu Ala Ala
    835             840             845

CGG AAC GTG CTG GTC AAG AGT CCC AAC CAT GTC AAA ATT ACA GAC TTC       2592
Arg Asn Val Leu Val Lys Ser Pro Asn His Val Lys Ile Thr Asp Phe
850             855             860

GGG CTG GCT CGG CTG CTG GAC ATT GAC GAG ACA GAG TAC CAT GCA GAT       2640
Gly Leu Ala Arg Leu Leu Asp Ile Asp Glu Thr Glu Tyr His Ala Asp
865             870             875             880

GGG GGC AAG GTG CCC ATC AAG TGG ATG GCG CTG GAG TCC ATT CTC CGC       2688
Gly Gly Lys Val Pro Ile Lys Trp Met Ala Leu Glu Ser Ile Leu Arg
                885             890             895

CGG CGG TTC ACC CAC CAG AGT GAT GTG TGG AGT TAT GGT GTG ACT GTG       2736
Arg Arg Phe Thr His Gln Ser Asp Val Trp Ser Tyr Gly Val Thr Val
            900             905             910

TGG GAG CTG ATG ACT TTT GGG GCC AAA CCT TAC GAT GGG ATC CCA GCC       2784
Trp Glu Leu Met Thr Phe Gly Ala Lys Pro Tyr Asp Gly Ile Pro Ala
```

-continued

```
                 915                 920                 925
CGG GAG ATC CCT GAC CTG CTG GAA AAG GGG GAG CGG CTG CCC CAG CCC       2832
Arg Glu Ile Pro Asp Leu Leu Glu Lys Gly Glu Arg Leu Pro Gln Pro
            930                 935                 940

CCC ATC TGC ACC ATT GAT GTC TAC ATG ATC ATG GTC AAA TGT TGG ATG       2880
Pro Ile Cys Thr Ile Asp Val Tyr Met Ile Met Val Lys Cys Trp Met
945                 950                 955                 960

ATT GAC TCT GAA TGT CGG CCA AGA TTC CGG GAG TTG GTG TCT GAA TTC       2928
Ile Asp Ser Glu Cys Arg Pro Arg Phe Arg Glu Leu Val Ser Glu Phe
                965                 970                 975

TCC CGC ATG GCC AGG GAC CCC CAG CGC TTT GTG GTC ATC CAG AAT GAG       2976
Ser Arg Met Ala Arg Asp Pro Gln Arg Phe Val Val Ile Gln Asn Glu
            980                 985                 990

GAC TTG GGC CCA GCC AGT CCC TTG GAC AGC ACC TTC TAC CGC TCA CTG       3024
Asp Leu Gly Pro Ala Ser Pro Leu Asp Ser Thr Phe Tyr Arg Ser Leu
        995                 1000                1005

CTG GAG GAC GAT GAC ATG GGG GAC CTG GTG GAT GCT GAG GAG TAT CTG       3072
Leu Glu Asp Asp Asp Met Gly Asp Leu Val Asp Ala Glu Glu Tyr Leu
    1010                1015                1020

GTA CCC CAG CAG GGC TTC TTC TGT CCA GAC CCT GCC CCG GGC GCT GGG       3120
Val Pro Gln Gln Gly Phe Phe Cys Pro Asp Pro Ala Pro Gly Ala Gly
1025                1030                1035                1040

GGC ATG GTC CAC CAC AGG CAC CGC AGC TCA TCT ACC AGG AGT GGC GGT       3168
Gly Met Val His His Arg His Arg Ser Ser Ser Thr Arg Ser Gly Gly
                1045                1050                1055

GGG GAC CTG ACA CTA GGG CTG GAG CCC TCT GAA GAG GAG GCC CCC AGG       3216
Gly Asp Leu Thr Leu Gly Leu Glu Pro Ser Glu Glu Glu Ala Pro Arg
            1060                1065                1070

TCT CCA CTG GCA CCC TCC GAA GGG GCT GGC TCC GAT GTA TTT GAT GGT       3264
Ser Pro Leu Ala Pro Ser Glu Gly Ala Gly Ser Asp Val Phe Asp Gly
        1075                1080                1085

GAC CTG GGA ATG GGG GCA GCC AAG GGG CTG CAA AGC CTC CCC ACA CAT       3312
Asp Leu Gly Met Gly Ala Ala Lys Gly Leu Gln Ser Leu Pro Thr His
    1090                1095                1100

GAC CCC AGC CCT CTA CAG CGG TAC AGT GAG GAC CCC ACA GTA CCC CTG       3360
Asp Pro Ser Pro Leu Gln Arg Tyr Ser Glu Asp Pro Thr Val Pro Leu
1105                1110                1115                1120

CCC TCT GAG ACT GAT GGC TAC GTT GCC CCC CTG ACC TGC AGC CCC CAG       3408
Pro Ser Glu Thr Asp Gly Tyr Val Ala Pro Leu Thr Cys Ser Pro Gln
                1125                1130                1135

CCT GAA TAT GTG AAC CAG CCA GAT GTT CGG CCC CAG CCC CCT TCG CCC       3456
Pro Glu Tyr Val Asn Gln Pro Asp Val Arg Pro Gln Pro Pro Ser Pro
            1140                1145                1150

CGA GAG GGC CCT CTG CCT GCT GCC CGA CCT GCT GGT GCC ACT CTG GAA       3504
Arg Glu Gly Pro Leu Pro Ala Ala Arg Pro Ala Gly Ala Thr Leu Glu
        1155                1160                1165

AGG CCC AAG ACT CTC TCC CCA GGG AAG AAT GGG GTC GTC AAA GAC GTT       3552
Arg Pro Lys Thr Leu Ser Pro Gly Lys Asn Gly Val Val Lys Asp Val
    1170                1175                1180

TTT GCC TTT GGG GGT GCC GTG GAG AAC CCC GAG TAC TTG ACA CCC CAG       3600
Phe Ala Phe Gly Gly Ala Val Glu Asn Pro Glu Tyr Leu Thr Pro Gln
1185                1190                1195                1200

GGA GGA GCT GCC CCT CAG CCC CAC CCT CCT CCT GCC TTC AGC CCA GCC       3648
Gly Gly Ala Ala Pro Gln Pro His Pro Pro Pro Ala Phe Ser Pro Ala
                1205                1210                1215

TTC GAC AAC CTC TAT TAC TGG GAC CAG GAC CCA CCA GAG CGG GGG GCT       3696
Phe Asp Asn Leu Tyr Tyr Trp Asp Gln Asp Pro Pro Glu Arg Gly Ala
            1220                1225                1230

CCA CCC AGC ACC TTC AAA GGG ACA CCT ACG GCA GAG AAC CCA GAG TAC       3744
```

```
                                        -continued
Pro Pro Ser Thr Phe Lys Gly Thr Pro Thr Ala Glu Asn Pro Glu Tyr
        1235                1240                1245
CTG GGT CTG GAC GTG CCA GTG TGA                                              3768
Leu Gly Leu Asp Val Pro Val
        1250            1255

(2) INFORMATION FOR SEQ ID NO:2:

(i) SEQUENCE CHARACTERISTICS:
        (A) LENGTH: 1255 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Leu Ala Ala Leu Cys Arg Trp Gly Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320
```

-continued

```
Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735
```

-continued

```
Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
            850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr Leu
            1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
            1075                1080                1085

Asp Leu Gly Met Gly Ala Ala Lys Gly Leu Gln Ser Leu Pro Thr His
            1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150
```

```
-continued

Arg Glu Gly Pro Leu Pro Ala Ala Arg Pro Ala Gly Ala Thr Leu Glu
            1155                1160                1165

Arg Pro Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
                1220                1225                1230

Pro Pro Ser Thr Phe Lys Gly Thr Pro Thr Ala Glu Asn Pro Glu Tyr
            1235                1240                1245

Leu Gly Leu Asp Val Pro Val
    1250                1255

(2) INFORMATION FOR SEQ ID NO:3:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:3:

TCTGGCGCGC TGGATGACGA TGACAAGAAA CGACGGCAGC AGAAGATC                    48

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:4:

TGAATTCTCG AGTCATTACA CTGGCACGTC CAGACCCAG                              39
```